United States Patent
Kehry et al.

(10) Patent No.: US 10,676,526 B2
(45) Date of Patent: Jun. 9, 2020

(54) FCRN ANTIBODIES AND METHODS OF USE THEREOF

(71) Applicant: Momenta Pharmaceuticals, Inc., Cambridge, MA (US)

(72) Inventors: Marilyn Kehry, San Diego, CA (US); David J. King, Encinitas, CA (US); Leona E. Ling, Winchester, MA (US); James Meador, III, Framingham, MA (US); Sucharita Roy, Tyngsboro, MA (US); Anthony Manning, Cambridge, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 179 days.

(21) Appl. No.: 15/546,870

(22) PCT Filed: Jan. 29, 2016

(86) PCT No.: PCT/US2016/015720
§ 371 (c)(1),
(2) Date: Jul. 27, 2017

(87) PCT Pub. No.: WO2016/123521
PCT Pub. Date: Aug. 4, 2016

(65) Prior Publication Data
US 2018/0016334 A1    Jan. 18, 2018

Related U.S. Application Data

(60) Provisional application No. 62/258,082, filed on Nov. 20, 2015, provisional application No. 62/110,071, filed on Jan. 30, 2015.

(51) Int. Cl.
| | | |
|---|---|---|
| *C07K 16/00* | (2006.01) | |
| *C12P 21/08* | (2006.01) | |
| *C07K 16/28* | (2006.01) | |
| *C07K 1/00* | (2006.01) | |
| *A61K 39/00* | (2006.01) | |

(52) U.S. Cl.
CPC ...... *C07K 16/283* (2013.01); *A61K 2039/505* (2013.01); *C07K 2317/33* (2013.01); *C07K 2317/41* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2011/0059101 A9 | 3/2011 | Kolkman et al. |
| 2014/0235482 A1 | 8/2014 | George et al. |
| 2014/0308206 A1 | 10/2014 | Sexton et al. |

FOREIGN PATENT DOCUMENTS

| | | |
|---|---|---|
| WO | WO 2007/087289 | 8/2007 |
| WO | WO 2009/131702 | 10/2009 |
| WO | WO 2012/167039 | 12/2012 |
| WO | WO 2014/019727 | 2/2014 |
| WO | WO 2014/204280 | 12/2014 |

OTHER PUBLICATIONS

Junghans and Anderson, "The protection receptor for IgG catabolism is the beta2-microglobulin-containing neonatal intestinal transport receptor," PNAS, May 1996, 93:5512-5516.
Christianson et al., "Monoclonal antibodies directed against human FcRn and their applications," MAbs, 2012, 4(2):208-216.
International Search Report and Written Opinion in International Application No. PCT/US16/15720, dated Jul. 26, 2016.
International Preliminary Report on Patentability in International Applications No. PCT/US2016/015720, dated Aug. 1, 2017.
Singapore Search Report and Written Opinion in Singapore Application No. 11201705475Q, dated Jul. 31, 2018.

*Primary Examiner* — Chun W Dahle
(74) *Attorney, Agent, or Firm* — Fish & Richardson P.C.

(57) ABSTRACT

The present invention features antibodies that have high binding affinity to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, and to treat immunological diseases (e.g., autoimmune diseases) in a subject.

19 Claims, 11 Drawing Sheets

Specification includes a Sequence Listing.

Human IgG Catabolism

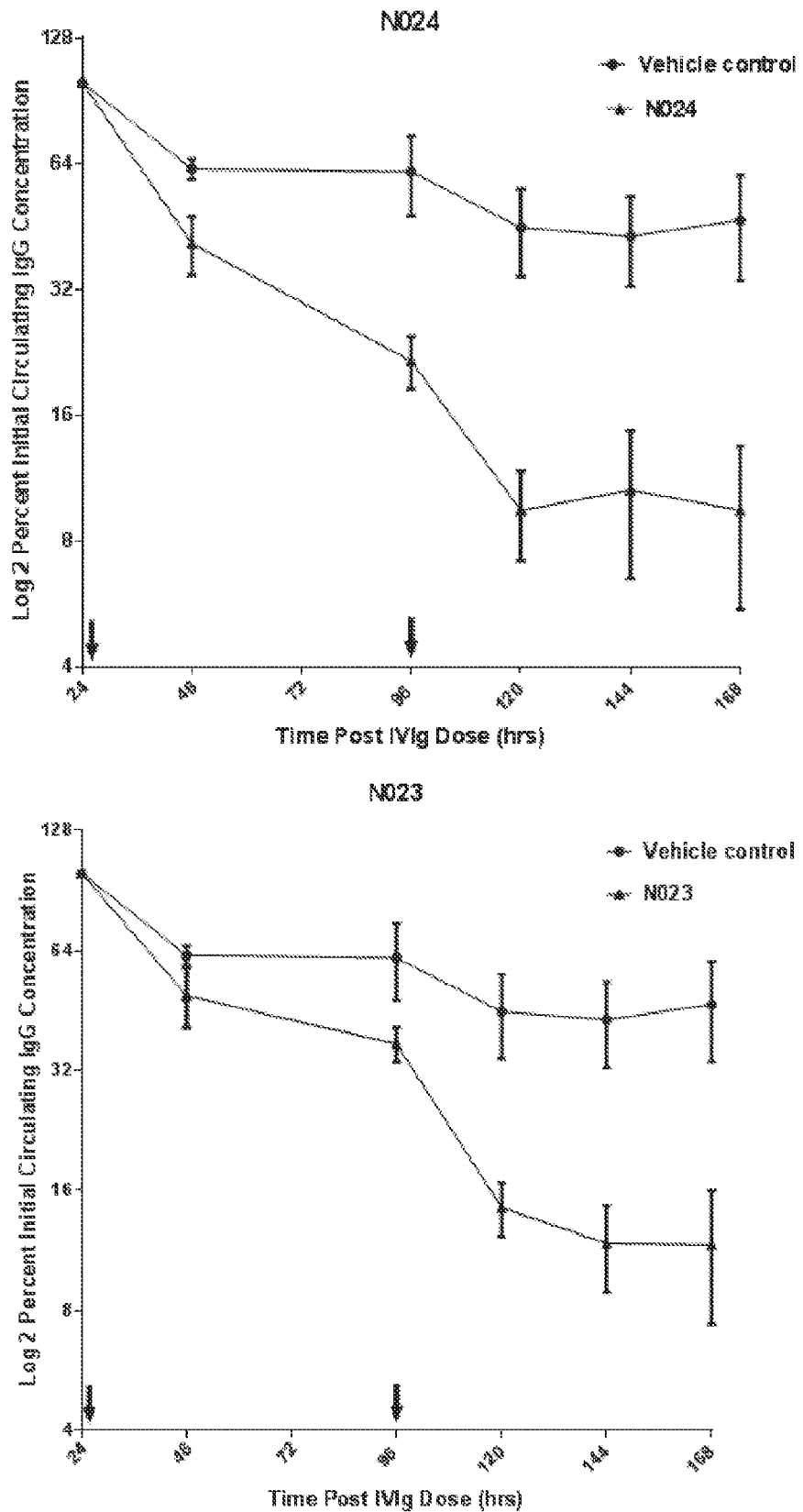
FIG. 2 Cont. Human IgG Catabolism

FCRN ANTIBODIES AND METHODS OF USE THEREOF

BACKGROUND OF THE INVENTION

Therapeutic proteins, e.g., therapeutic antibodies, have rapidly become a clinically important drug class for patients with immunological diseases.

SUMMARY OF THE INVENTION

The present invention features novel antibodies to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, or to treat immunological diseases (e.g., autoimmune diseases) in a subject.

In one aspect, the invention features an isolated antibody that binds to human FcRn. The isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 has a sequence having no more than two amino acid substitutions relative to the sequence of TGTGSDVGSYNLVS (SEQ ID NO: 1), the CDR L2 has a sequence having no more than one amino acid substitutions relative to the sequence of GDSERPS (SEQ ID NO: 2), the CDR L3 has a sequence having no more than one amino acid substitutions relative to the sequence of SSYAGSGIYV (SEQ ID NO: 3), the CDR H1 has a sequence having no more than one amino acid substitutions relative to the sequence of TYAMG (SEQ ID NO: 4), DYAMG (SEQ ID NO: 5), or NYAMG (SEQ ID NO: 6), the CDR H2 has a sequence having no more than two amino acid substitutions relative to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 has a sequence having no more than one amino acid substitutions relative to the sequence of LAIGDSY (SEQ ID NO: 11).

In some embodiments, the antibody binds human FcRn with a $K_D$ of less than 200, 150, 100, 50, or 40 pM.

In some embodiments, the antibody binds human FcRn with a $K_D$ that is less than or equal to that of an antibody having the light chain variable region and heavy chain variable region of N022, N023, N024, N026, or N027, and further having the same Fc region as that of the antibody to which it is being compared.

In another aspect, the invention features an isolated antibody containing: (1) a light chain variable region that includes a CDR L1, a CDR L2, and a CDR L3 and (2) a heavy chain variable region that includes a CDR H1, a CDR H2, and a CDR H3, wherein the CDR L1 has the sequence of $X_1$GTGSDVGSYN$X_2$VS (SEQ ID NO: 12), the CDR L2 has the sequence of GD$X_3X_4$RPS (SEQ ID NO: 13), the CDR L3 has the sequence of $X_5$SY$X_6$GSGIYV (SEQ ID NO: 14), the CDR H1 has the sequence of $Z_1$YAMG (SEQ ID NO: 15), the CDR H2 has the sequence of SIG$Z_2$SG$Z_3$QT$Z_4$YADS (SEQ ID NO: 16), and the CDR H3 has the sequence of LA$Z_5Z_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, and $Z_6$ is G, S, D, Q, or H, and wherein the antibody binds human FcRn with a $K_D$ that is less than or equal to that of antibody having the light chain variable region and heavy chain variable region of N026 and further having the same Fc region as the antibody being compared. In some embodiments, $X_1$ is T, A, S, or I. In other embodiments, $X_2$ is L or I. In some embodiments, $X_3$ is S, N, or T. In still other embodiments, $X_4$ is Q, E, or N, $X_5$ is C, S, I, or Y. In some embodiments, $X_6$ is A or V, $Z_1$ is E, T, D, or N. In further embodiments, $Z_2$ is S or A. In some embodiments, $Z_4$ is K or R. In yet other embodiments, $Z_5$ is I, L, or H.

In another aspect, the invention features an isolated antibody containing a light chain variable region that includes a CDR L1 having the sequence of TGTGSDVGSYNLVS (SEQ ID NO: 1), a CDR L2 having the sequence of GDSERPS (SEQ ID NO: 2), and a CDR L3 having the sequence of SSYAGSGIYV (SEQ ID NO: 3), and a heavy chain variable region that includes a CDR H1 having the sequence of $Z_1$YAMG (SEQ ID NO: 15), a CDR H2 having the sequence of SIG$Z_2$SG$Z_3$QTRYADS (SEQ ID NO: 18), and a CDR H3 having the sequence of LAIGDSY (SEQ ID NO: 11), wherein $Z_1$ is T, D, or N, $Z_2$ is S or A, and $Z_3$ is G, S or A.

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGSSGAQTRYADS (SEQ ID NO: 7), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of DYAMG (SEQ ID NO: 5), a CDR H2 having the sequence of SIGASGSQTRYADS (SEQ ID NO: 8), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of NYAMG (SEQ ID NO: 6), a CDR H2 having the sequence of SIGASGAQTRYADS (SEQ ID NO: 9), and a CDR H3 having the sequence of LAIGDSY (SEQ ID NO: 11).

In other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGGQTRYADS (SEQ ID NO: 10), and a CDR H3 having the sequence of LAIGDSY (SEQ ID NO: 11).

In yet other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGSQTRYADS (SEQ ID NO: 8), and a CDR H3 having the sequence of LAIGDSY (SEQ ID NO: 11).

In some embodiments, the light chain variable region of the isolated antibody of the invention has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS.

In some embodiments, the heavy chain variable region of the isolated antibody of the invention has a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain variable region of the isolated antibody of the invention has a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain variable region of the isolated antibody of the invention has a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain variable region of the isolated antibody of the invention has a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain variable region of the isolated antibody of the invention has a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain variable region and a heavy chain variable region, wherein the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain variable region and a heavy chain variable region, wherein the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain variable region and a heavy chain variable region, wherein the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain variable region and a heavy chain variable region, wherein the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In yet another aspect, the invention features an isolated antibody containing a light chain variable region and a heavy chain variable region, wherein the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain variable region of the isolated antibody of the invention has a sequence having at least 95%, 97%, 99%, or 100% identity to the sequence of any one of SEQ ID NOs: 20-24. In other embodiments, the light chain variable region of the isolated antibody of the invention has a sequence having at least 95%, 97%, 99%, or 100% identity to the sequence of SEQ ID NO: 19.

In some embodiments, the isolated antibody of the invention further includes amino acid substitution N297A, relative to the sequence of any one of SEQ ID NOs: 20-24.

In other embodiments, the isolated antibody further includes amino acid substitutions D355E and L357M, relative to the sequence of any one of SEQ ID NOs: 20-24.

In other embodiments, the isolated antibody of the invention further includes any one or more of the following amino acid substitutions: A23V, S30R, L80V, A84T, E85D, A93V, relative to the sequence of any one of SEQ ID NOs: 20-24 and Q38H, V58I, and G99D, relative to the sequence of SEQ ID NO: 19.

In yet other embodiment, the isolated antibody of the invention does not contain a C-terminal lysine at residue 446, relative to the sequence of any one of SEQ ID NOs: 20-24.

In some embodiments, the antibody of any of the above aspects binds human FcRn with a $K_D$ that is less than or equal to that of an antibody having the light chain variable region and heavy chain variable region of N022, N023, N024, N026, or N027 and also having the same Fc region as that of the antibody being compared. For example, in a particular $K_D$ assay, the $K_D$ of the antibody is less than 200, 150, 100, 50, or 40 pM.

The amino acid positions assigned to complementary determining regions (CDRs) and framework regions (FRs) of any isolated antibody described herein are defined according to EU index of Kabat (Sequences of Proteins of Immunological Interest, 5th Ed. Public Health Service, National Institutes of Health, Bethesda, Md. (1991)).

In another aspect, the invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

-continued
```
VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

In another aspect, the invention features an isolated antibody containing a light chain variable region and a heavy chain variable region, wherein the light chain variable region has the sequence of

```
                                          (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
``` and the heavy chain variable region has the sequence of

```
                                          (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

In another aspect, the invention features an isolated antibody containing a light chain variable region and a heavy chain variable region, wherein the light chain variable region has the sequence of

```
                                          (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
``` and the heavy chain variable region has the sequence of

```
                                          (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

In yet another aspect, the invention features an isolated antibody containing a light chain variable region and a heavy chain variable region, wherein the light chain variable region has the sequence of

```
                                          (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
``` and the heavy chain variable region has the sequence of

```
                                          (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

In some embodiments of any of the above aspects, the isolated antibody of the invention is a monoclonal antibody. In some embodiments, the isolated antibody is IgG1. In some embodiments, the isolated antibody includes a λ light chain. In some embodiments, the isolated antibody includes a kappa light chain. In some embodiments, the glycosylation site on the Fc region of the isolated antibody is sialylated (e.g., disialylated).

In some embodiments of any of the above aspects, the isolated antibody of the invention is a humanized or fully human antibody.

In some embodiments, the isolated antibody binds to human FcRn with a $K_D$ of 1-100, 5-150, 5-100, 5-75, 5-50, 10-50, or 10-40 pM.

In some embodiments, the isolated antibody of the invention binds rodent, e.g., mouse or rat FcRn. In some embodiments, the isolated antibody of the invention binds rodent, e.g., mouse or rat, FcRn with a $K_D$ of less than 200, 150, 100, 50, or 40 pM.

In another aspect, the invention features a nucleic acid molecule encoding any isolated antibody described herein.

In yet another aspect, the invention features a vector containing a nucleic acid molecule encoding any antibody described herein.

In another aspect, the invention features a host cell that expresses any isolated antibody described herein. The host cell includes a nucleic acid molecule encoding any isolated antibody described herein or a vector containing a nucleic acid molecule encoding any isolated antibody described herein, wherein the nucleic acid molecule or vector is expressed by the host cell.

In some embodiments, the host cell is a Chinese hamster ovary (CHO) cell. In some embodiment, the host cell is an Sp2 cell or NS0 cell.

In another aspect, the invention features a method of preparing any isolated antibody described herein. The method includes: a) providing a host cell that includes a nucleic acid molecule encoding any isolated antibody described herein or a vector containing a nucleic acid molecule encoding any isolated antibody described herein, and b) expressing the nucleic acid molecule or vector in the host cell under conditions that allow for the formation of the antibody.

In some embodiments, the method includes the step of recovering the antibody from the host cell, e.g., at a concentration of about 1-100, 1-50, 1-25, 2-50, 5-50, or 2-20 mg/ml.

In other embodiments, the host cell used in the method is a CHO cell.

In another aspect, the invention features a pharmaceutical composition including any isolated antibody described herein and one or more pharmaceutically acceptable carriers or excipients.

In some embodiments, the pharmaceutical composition includes the antibody in a therapeutically effective dose amount.

In another aspect, the invention features a method of increasing IgG catabolism in a subject. In another aspect, the invention features a method of reducing autoantibodies in a subject. In yet another aspect, the invention features a method of treating or reducing an immune complex-based activation of an immune response in a subject. The methods include administering to the subject any isolated antibody described herein or a pharmaceutical composition including any isolated antibody described herein.

In some embodiments, the immune response in the subject is an acute or chronic immune response.

In some embodiments, the subject has or the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dilated cardiomyopathy, and serum sickness.

In some embodiments, the subject has or the chronic immune response is activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis.

In some embodiments, the subject has or the immune response is activated by an autoimmune disease. In particular, the autoimmune disease is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

Definitions

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit FcRn antigen-binding activity.

"Antibody fragments" comprise a portion of an intact antibody, preferably the antigen binding or variable region of the intact antibody. Examples of antibody fragments include Fab, Fab', F(ab')$_2$, and Fv fragments, diabodies, linear antibodies, single-chain antibody molecules, and multispecific antibodies.

As used herein, the term "isolated antibody" refers to an antibody which has been separated and/or recovered from a component of its manufacturing host cell environment. Contaminant components of its manufacturing host cell environment are materials which would interfere with research, diagnostic, or therapeutic uses of the antibody. Contaminant components may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or non-reducing conditions using, for example, Coomassie blue or silver stain. An isolated antibody includes the antibody in situ within recombinant cells. Ordinarily, however, an isolated antibody will be prepared by at least one purification step. A pharmaceutical preparation of an isolated antibody typically has less than 250 ppm (e.g., less than 200 ppm, 150 ppm. 100 ppm) of host cell proteins (HCP) as determined by an ELISA based HCP assay performed as recommended by an FDA "Guidance for Industry" document.

As used herein, the term "monoclonal antibody" refers to an antibody obtained from a population of substantially homogeneous antibodies, i.e., individual antibodies in the population have the same primary sequence except for possible naturally occurring mutations that may be present in minor amounts. Monoclonal antibodies are highly specific and directed against a single antigenic site (i.e., an epitope on human FcRn). In contrast to polyclonal antibody preparations which typically include different antibodies directed against different epitopes, each monoclonal antibody is directed against a single epitope on the antigen. The modifier "monoclonal" indicates the character of the antibody as being obtained from a substantially homogenous population of antibodies, and is not to be construed as requiring production of the antibody by any particular method.

As used herein, the terms "variable region" and "variable domain" refer to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs). According to the methods used in this invention, the amino acid positions assigned to CDRs and FRs are defined according to Kabat (Sequences of Proteins of Immunological Interest, 5th Ed. Public Health Service, National Institutes of Health, Bethesda, Md. (1991)). Using this numbering system, the actual linear amino acid sequence may contain fewer or additional amino acids corresponding to a shortening of, or insertion into, a CDR (defined further herein) or FR (defined further herein) of the variable region. For example, a heavy chain variable region may include a single inserted residue (i.e., residue 52a according to Kabat) after residue 52 of CDR H2 and inserted residues (i.e., residues 82a, 82b, 82c, etc. according to Kabat) after residue 82 of heavy chain FR. The Kabat numbering of residues may be determined for a given antibody by alignment at regions of homology of the sequence of the antibody with a "standard" Kabat numbered sequence.

As used herein, the terms "complementary determining regions" and "CDRs" refer to the regions of an antibody variable domain which are hypervariable in sequence and/or form structurally defined loops. A CDR is also known as a hypervariable region. The light chain and heavy chain variable regions each has three CDRs. The light chain variable region contains CDR L1, CDR L2, and CDR L3. The heavy chain variable region contains CDR H1, CDR H2, and CDR H3. Each CDR may include amino acid residues from a complementarity determining region as defined by Kabat (i.e. about residues 24-34 (CDR L1), 50-56 (CDR L2) and 89-97 (CDR L3) in the light chain variable region and about residues 31-35 (CDR H1), 50-65 (CDR H2) and 95-102 (CDR H3) in the heavy chain variable region.

As used herein, the term "FcRn" refers a neonatal Fc receptor that binds to the Fc region of an IgG antibody, e.g., an IgG1 antibody. An exemplary FcRn is human FcRn having UniProt ID No. P55899. Human FcRn is believed to be responsible for maintaining the half-life of IgG by binding and trafficking constitutively internalized IgG back to the cell surface for the recycling of IgG.

As used herein, the terms "affinity" and "binding affinity" refer to the strength of the binding interaction between two molecules. Generally, binding affinity refers to the strength of the sum total of non-covalent interactions between a single binding site of a molecule and its binding partner, such as an isolated antibody and its target (e.g., an isolated anti-FcRn antibody of the invention and a human FcRn). Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. One method for determining the $K_D$ of an antibody to human FcRn is described in Example 2 ("the SPR method"). Using this method the $K_D$ of N022, N023, N024, N026, and N027 was 31, 31.4, 35.5, 36.5, and 19.3 pM, respectively.

As used herein, the term "inhibit IgG binding to FcRn" refers to the ability of an anti-FcRn antibody of the invention to block or inhibit the binding of IgG (e.g., IgG1) to human FcRn. In some embodiments, an anti-FcRn antibody of the invention binds FcRn, for example, at the site on human FcRn to which IgG binds. Thus, the anti-FcRn antibody of the invention is able to inhibit the binding of IgG (e.g., a subject's autoantibodies) to FcRn. In some embodiments, the molecule (e.g., an anti-FcRn antibody of the invention) substantially or completely inhibits binding to IgG. In some embodiments, the binding of IgG is reduced by 10%, 20%, 30%, 50%, 70%, 80%, 90%, 95%, or even 100%.

As used herein, the term "hydrophobic amino acid" refers to an amino acid having relatively low-water solubility. Hydrophobic amino acids include, but are not limited to, leucine, isoleucine, alanine, phenylalanine, valine, and proline. Particularly preferred hydrophobic amino acids in the present invention are alanine, leucine, isoleucine, and valine.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids include, but are not limited to, serine, threonine, cysteine, methionine, tyrosine, tryptophan, asparagine, and glutamine. Particularly preferred polar amino acids in the present invention are serine, threonine, asparagine, glutamine, cysteine, and tyrosine.

As used herein, the term "acidic amino acid" refers to an amino acid whose side chain contains a carboxylic acid group having a pKa between 3.5 and 4.5. Acidic amino acids include, but are not limited to, aspartic acid and glutamic acid.

As used herein, the term "basic amino acid" refers to an amino acid whose side chain contains an amino group having a pKa between 9.5 and 13. Basic amino acids include, but are not limited to, histidine, lysine, and arginine.

As used herein, the term "percent (%) identity" refers to the percentage of amino acid (or nucleic acid) residues of a candidate sequence, e.g., an anti-FcRn antibody of the invention, that are identical to the amino acid (or nucleic acid) residues of a reference sequence, e.g., a wild-type anti-FcRn antibody, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid)

sequence identity to, with, or against a given reference sequence) is calculated as follows:

$$100\times(\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (e.g., transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding anti-FcRn antibodies of the invention.

As used herein, the term "vector" refers to a nucleic acid molecule capable of transporting another nucleic acid molecule to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

As used herein, the term "pharmaceutical composition" refers to a medicinal or pharmaceutical formulation that contains an active ingredient as well as one or more excipients and diluents to enable the active ingredient suitable for the method of administration. The pharmaceutical composition of the present invention includes pharmaceutically acceptable components that are compatible with the anti-FcRn antibody. The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present invention, the pharmaceutically acceptable carrier must provide adequate pharmaceutical stability to the Fc construct. The nature of the carrier differs with the mode of administration. For example, for intravenous administration, an aqueous solution carrier is generally used; for oral administration, a solid carrier is preferred.

As used herein, the term "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

DETAILED DESCRIPTION OF THE INVENTION

Figure 1:
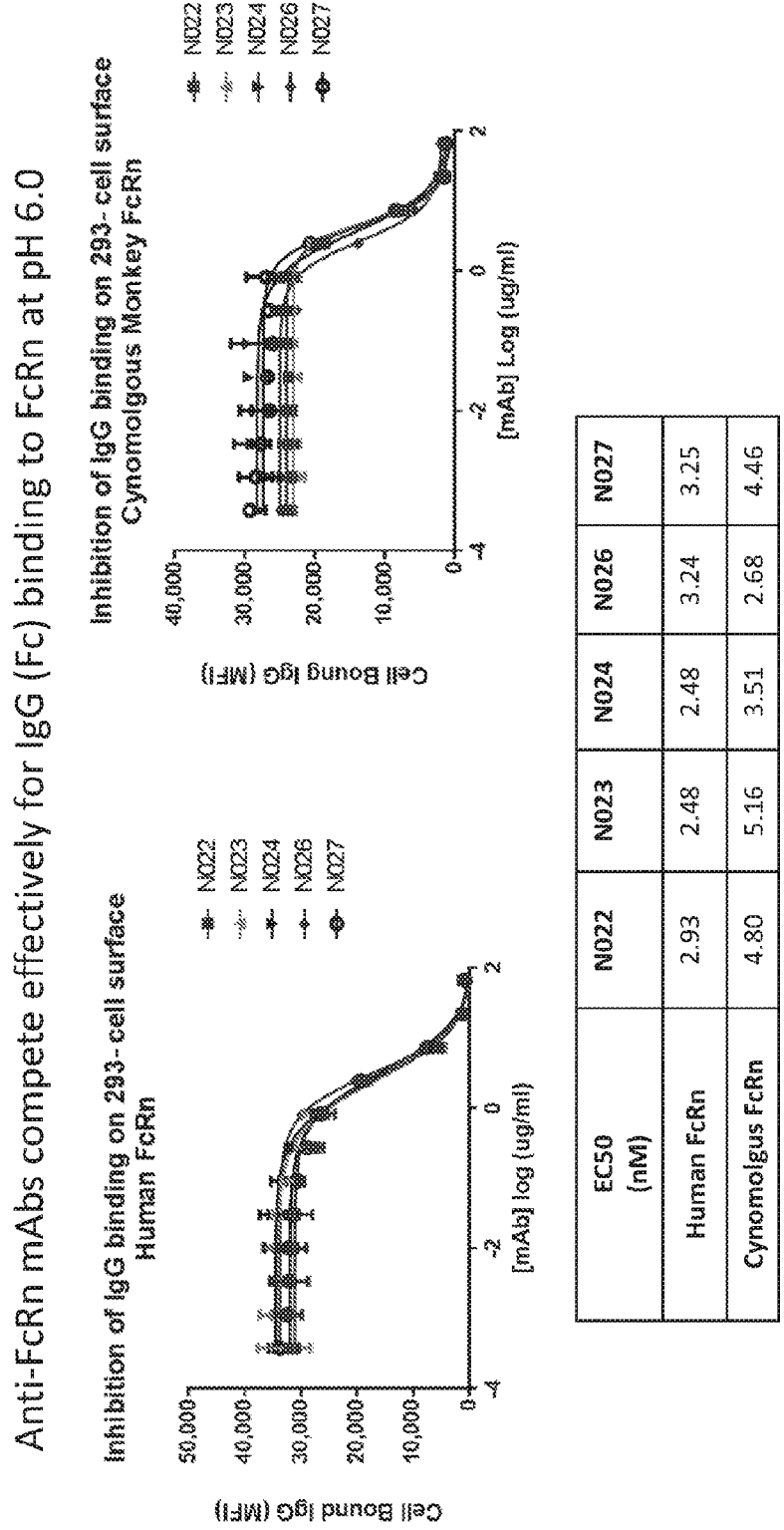
FIG. 1 includes two graphs and a table that show IgG competitive binding of antibodies N022-N024, N026, and N027 to human or cynomolgus monkey FcRn at pH 6.0.

The present invention features isolated antibodies that bind to human neonatal Fc receptor (FcRn) with high affinity. The present invention features anti-FcRn antibodies, methods and compositions for preparing anti-FcRn antibodies, and methods for blocking FcRn activity, reducing immune complex-based activation of an immune response, and treating immunological diseases.

I. Anti-FcRn Antibodies

In general, the invention features isolated antibodies that bind to the human FcRn with high affinity. An anti-FcRn antibody of the invention refers to an antibody that can bind to human FcRn and inhibit IgG (e.g., IgG autoantibodies) binding to FcRn. In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment, e.g., a Fab, Fab', Fab'-SH, F(ab')$_2$, or scFv.

In some embodiments, the antibody is a chimeric antibody. For example, an antibody contains antigen binding sequences from a non-human donor grafted to a heterologous non-human, human, or humanized sequence (e.g., framework and/or constant domain sequences). In one embodiment, the non-human donor is a mouse. In another embodiment, an antigen binding sequence is synthetic, e.g., obtained by mutagenesis (e.g., phage display screening, etc.). In a further embodiment, a chimeric antibody has non-human (e.g., mouse) variable regions and human constant regions. In one example, a mouse light chain variable region is fused to a human κ light chain. In another example, a mouse heavy chain variable region is fused to a human IgG1 constant region.

In one aspect, the invention features an isolated antibody capable of binding to human FcRn. The isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 has a sequence having at least 92% identity to the sequence of TGTGSDVGSYNLVS (SEQ ID NO: 1), the CDR L2 has a sequence having at least 85% identity to the sequence of GDSERPS (SEQ ID NO: 2), the CDR L3 has a sequence having at least 90% identity to the sequence of SSYAGSGIYV (SEQ ID NO: 3), the CDR H1 has a sequence having at least 80% identity to the sequence of TYAMG (SEQ ID NO: 4), DYAMG (SEQ ID NO: 5), or NYAMG (SEQ ID NO: 6), the CDR H2 has a sequence having at least 92% identity to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 has a sequence having at least 85% identity to the sequence of LAIGDSY (SEQ ID NO: 11). In some embodiments, the antibody binds human FcRn with a $K_D$ of less than 200, 150, 100, 50, or 40 pM. In some embodiments, the antibody binds human FcRn with a $K_D$ that is less than or equal to that of an antibody having the light chain variable region and heavy chain variable region of N022, N023, N024, N026, or N027, and further having the same Fc region as the antibody being compared.

In some embodiments, an isolated antibody of the invention has a CDR L1 that has the sequence of $X_1$GTGSDVGSYNX$_2$VS (SEQ ID NO: 12), a CDR L2 that has the sequence of GDX$_3$X$_4$RPS (SEQ ID NO: 13), a CDR L3 that has the sequence of X$_5$SYX$_6$GSGIYV (SEQ ID NO: 14), a CDR H1 that has the sequence of Z$_1$YAMG (SEQ ID NO: 15), a CDR H2 that has the sequence of SIGZ$_2$SGZ$_3$QTZ$_4$YADS (SEQ ID NO: 16), and a CDR H3 that has the sequence of LAZ$_5$Z$_6$DSY (SEQ ID NO: 17), where $X_1$ is a polar or hydrophobic amino acid (e.g., preferably T, A, S, or I), $X_2$ is a hydrophobic amino acid (e.g., preferably L or I), $X_3$ is a polar amino acid (e.g., preferably S, N, or T), $X_4$ is a polar or acidic amino acid (e.g., preferably Q, E, or N), $X_5$ is a polar or hydrophobic amino acid (e.g., preferably C, S, I, or Y), $X_6$ is a hydrophobic amino acid (e.g., preferably A or V), $Z_1$ is a polar or acidic amino acid (e.g., preferably E, T, D, or N), $Z_2$ is a polar or hydrophobic amino acid (e.g., preferably S or A), $Z_3$ is G, S, or A, $Z_4$ is a basic amino acid (e.g., preferably K or R), $Z_5$ is a hydrophobic or basic amino acid (e.g., preferably I, L, or H), and $Z_6$ is G, S, D, Q, or H, and where the antibody binds human FcRn with a $K_D$ of less than 200, 150, 100, 50, or 40 pM.

In other embodiments, an isolated antibody of the invention has a CDR L1 that has the sequence of TGTGSDVGSYNLVS (SEQ ID NO: 1), a CDR L2 that has the sequence of GDSERPS (SEQ ID NO: 2), a CDR L3 that has the sequence of SSYAGSGIYV (SEQ ID NO: 3), a CDR H1 that has the sequence of Z$_1$YAMG (SEQ ID NO: 15), a CDR H2 that has the sequence of SIGZ$_2$SGZ$_3$QTRYADS (SEQ ID NO: 18), and a CDR H3 that has the sequence of LAIGDSY (SEQ ID NO: 11), where $Z_1$ is T, D, or N, $Z_2$ is S or A, and $Z_3$ is G, S or A.

Table 1 shows the amino acid sequences of the light and heavy chain complementary determining regions (CDRs) of some exemplary anti-FcRn antibodies of the invention.

TABLE 1

| Anti-FcRn antibody | CDR L1 | CDR L2 | CDR L3 | CDR H1 | CDR H2 | CDR H3 |
|---|---|---|---|---|---|---|
| N022 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGSSGAQTRYADS (SEQ ID NO: 7) | LAIGDSY (SEQ ID NO: 11) |
| N023 | TGTGSDVGSYNLVS (SEQ ID NO: 1) | GDSERPS (SEQ ID NO: 2) | SSYAGSGIYV (SEQ ID NO: 3) | DYAMG (SEQ ID NO: 5) | SIGASGSQTRYADS (SEQ ID NO: 8) | LAIGDSY (SEQ ID NO: 11) |
| N024 | TGTGSDVGSYNLVS (SEQ ID NO: 1) | GDSERPS (SEQ ID NO: 2) | SSYAGSGIYV (SEQ ID NO: 3) | NYAMG (SEQ ID NO: 6) | SIGASGAQTRYADS (SEQ ID NO: 9) | LAIGDSY (SEQ ID NO: 11) |
| N026 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGASGGQTRYADS (SEQ ID NO: 10) | LAIGDSY (SEQ ID NO: 11) |
| N027 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGASGSQTRYADS (SEQ ID NO: 8) | LAIGDSY (SEQ ID NO: 11) |

Table 2 shows the SEQ ID NOs of the light and heavy chain variable regions of these exemplary anti-FcRn antibodies of the invention.

TABLE 2

| Anti-FcRn antibody | Light Chain Variable Region | Heavy Chain Variable Region |
|---|---|---|
| N022 | SEQ ID NO: 19 | SEQ ID NO: 20 |
| N023 |  | SEQ ID NO: 21 |
| N024 |  | SEQ ID NO: 22 |
| N026 |  | SEQ ID NO: 23 |
| N027 |  | SEQ ID NO: 24 |

In some embodiments, the light chain variable region of an isolated antibody of the invention has a sequence having at least 90% identity to the sequence of (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS.

In some embodiments, the heavy chain variable region of an isolated antibody of the invention has a sequence having at least 90% identity to the sequence of (SEQ ID NO: 20)
EVQLLESGGGLVQPGGSLRLSCAASGFTFSTYAMGWVRQAPGKGLEWVSS
IGSSGAQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG.

In some embodiments, the heavy chain variable region of an isolated antibody of the invention has a sequence having at least 90% identity to the sequence of (SEQ ID NO: 21)
EVQLLESGGGLVQPGGSLRLSCAASGFTFSDYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG.

In some embodiments, the heavy chain variable region of an isolated antibody of the invention has a sequence having at least 90% identity to the sequence of (SEQ ID NO: 22)
EVQLLESGGGLVQPGGSLRLSCAASGFTFSNYAMGWVRQAPGKGLEWVSS
IGASGAQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

In other embodiments, the heavy chain variable region of an isolated antibody of the invention has a sequence having at least 90% identity to the sequence of (SEQ ID NO: 23)
EVQLLESGGGLVQPGGSLRLSCAASGFTFSTYAMGWVRQAPGKGLEWVSS
IGASGGQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

In yet other embodiments, the heavy chain variable region of an isolated antibody of the invention has a sequence having at least 90% identity to the sequence of (SEQ ID NO: 24)
EVQLLESGGGLVQPGGSLRLSCAASGFTFSTYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

The invention features an isolated antibody including a light chain variable region and a heavy chain variable region, where the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain variable region and a heavy chain variable region, where the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain variable region and a heavy chain variable region, where the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain variable region and a heavy chain variable region, where the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

-continued

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain variable region and a heavy chain variable region, where the light chain variable region has a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

Furthermore, in any of the anti-FcRn antibodies described herein, the heavy chain variable region of the antibody has a sequence having at least 95%, 97%, 99%, or 100% identity to the sequence of any one of SEQ ID NOs: 20-24. In any of the anti-FcRn antibodies described herein, the light chain variable region has a sequence having at least 95%, 97%, 99%, or 100% identity to the sequence of SEQ ID NO: 19.

The antibodies of the invention may further contain amino acid substitutions, additions, and/or deletions outside of the CDRs (i.e., in framework regions (FRs)). In some embodiments, the antibodies of the invention may further include any one or more of the following amino acid substitutions: A23V, S30R, L80V, A84T, E85D, A93V, relative to the sequence of any one of SEQ ID NOs: 20-24, and Q38H, V58I, and G99D, relative to the sequence of SEQ ID NO: 19.

In some embodiments, the antibodies of the invention may include amino acid substitutions, additions, and/or deletions in the constant regions (e.g., Fc region) of the antibody that, e.g., lead to decreased effector function, e.g., decreased complement-dependent cytolysis (CDC), antibody-dependent cell-mediated cytolysis (ADCC), and/or antibody-dependent cell-mediated phagocytosis (ADCP), and/or decreased B-cell killing. The constant regions are not involved directly in binding an antibody to its target, but exhibit various effector functions, such as participation of the antibody in antibody-dependent cellular toxicity. In some embodiments, the antibodies of the invention are characterized by decreased binding (i.e., absence of binding) to human complement factor C1q and/or human Fc receptor on natural killer (NK) cells. In other embodiments, the antibodies of the invention are characterized by decreased binding (i.e., absence of binding) to human FcγRI, FcγRIIA, and/or FcγRIIIA. To alter or reduce an antibody-dependent effector function, such as CDC, ADCC, ADCP, and/or B-cell killing, antibodies of the invention may be of the IgG class and contain one or more amino acid substitutions E233, L234, G236, D265, D270, N297, E318, K320, K322, A327, A330, P331, and/or P329 (numbering according to the EU index of Kabat (Sequences of Proteins of Immunological Interest, 5th Ed. Public Health Service, National Institutes of Health, Bethesda, Md. (1991))). In some embodiments, the antibodies contain the mutations L234A/L235A or D265A/N297A. Preferably, an anti-FcRn antibody of the invention contains amino acid substitution N297A, relative to the sequence of any one of SEQ ID NOs: 20-24, such that the antibody of the invention is changed to an aglycosylated form. The resulting effectorless antibody shows very little binding to complement or Fc receptors (i.e., complement C1q binding), indicating low CDC potential.

In other embodiments, the antibodies of the invention may include those having specific amino acid changes that improve stability of the antibody.

Moreover, in other embodiments, to minimize potential immunogenicity, some antibodies of the invention, e.g., N024, N026, and N027, may undergo an allotype change from G1m17.1 to G1m17 by substituting amino acids D355 and L357 (relative to the sequence of any one of SEQ ID NOs: 20-24) to glutamic acid and methionine, respectively.

In other embodiments, the antibodies of the invention, e.g., N022-N024, N026, and N027, do not contain a C-terminal lysine at residue 446, relative to the sequence of any one of SEQ ID NOs: 20-24.

The invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain variable region and a heavy chain variable region, wherein the light chain variable region has the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain variable region has the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

-continued

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In yet other embodiments, the antibodies of the invention are sialylated antibodies.

In any of the anti-FcRn antibodies described herein, in some embodiments, the antibody binds mouse or rat FcRn with a $K_D$ of less than 200, 150, 100, 50, or 40 pM.

In any of the anti-FcRn antibodies described herein, in some embodiments, the antibody binds to human FcRn with an affinity of between 1-100, 5-150, 5-100, 5-75, 5-50, 10-50, or 10-40 pM.

The anti-FcRn antibodies of the invention may be of immunoglobulin antibody isotype IgG, IgE, IgM, IgA, or IgD. Preferably, the anti-FcRn antibodies are of immunoglobulin antibody isotype IgG. The anti-FcRn antibodies may also be of any immunoglobulin antibody isotype subclasses. For example, the anti-FcRn antibodies may be of IgG subclass IgG1, IgG2, IgG3, or IgG4. Preferably, the anti-FcRn antibodies are of subclass IgG1. In particular, the anti-FcRn antibodies of the invention contain an IgG G1 m17 or G1m17.1 allotype heavy chain. In some embodiments, the light chain of the anti-FcRn antibodies may be a κ light chain, a λ light chain, or a κ-λ chimeric light chain. In preferred embodiments, the anti-FcRn antibodies of the invention contain a full-length λ light chain.

In some embodiments, the antibodies of the invention are monoclonal. The antibodies of the invention may also be polyclonal, chimeric, humanized or fully human. In some embodiments, the antibody of the invention may be affinity matured. In other embodiments, the antibody of the invention may be an antibody fragment.

Without being bound by theory, it is believed that the anti-FcRn antibodies of the invention compete with and inhibit the binding of IgG to human FcRn. Epitope mapping by hydrogen-deuterium exchange of the antibodies of the invention indicates that the antibodies bind to an epitope on FcRn located in and/or adjacent to the Fc-FcRn interaction interface, which suggests that the antibodies of the invention block IgG binding to FcRn by direction inhibition. Furthermore, the epitope-mapped binding site is distant from the albumin-binding site of FcRn. Accordingly, serum albumin-binding should not be inhibited and serum albumin levels should not be decreased. Indeed, experimental evidence shows mouse albumin levels remained constant after anti-FcRn antibody administration, indicating that albumin recycling is not disturbed by antibody binding to FcRn.

II. Sialylated Anti-FcRn Antibodies

In some embodiments, the glycosylation site of the Fc region of anti-FcRn antibodies of the invention is at least 25%, 50%, 75% or more sialylated, on a mole basis. The antibodies of the invention may be sialylated with a sialyl-transferase (ST6 Gal-I), which sialylates a substrate in an ordered fashion. Specifically, under certain conditions, ST6 sialyltransferase catalyzes addition of a sialic acid on the α1,3 arm of glycans on the Fc region of anti-FcRn antibodies, followed by addition of a second sialic acid on the α1,6 arm, followed by removal of sialic acid from the α1,3 arm.

Isolated anti-FcRn antibodies of the invention may be sialylated during production in the manufacturing host cells (e.g., mammalian cells, e.g., mammalian cells co-transfected with—or overexpressing—an ST6 sialyltransferase). In other embodiments, isolated anti-FcRn antibodies of the invention may be sialylated in vitro, post purification from the manufacturing host cell, e.g., enzymatically or through chemical conjugation. Methods of producing sialylated anti-FcRn antibodies are described in PCT Publication WO2014/179601.

III. FcRn Inhibition

FcRn is a type I transmembrane protein that functions as an IgG- and serum albumin-binding, intracellular vesicular trafficking protein. FcRn is expressed in endothelial cells, luminal epithelial cells, hepatocytes, podocytes, granulocytes, monocytes, macrophages, dendritic cells, and NK cells, but not on B or T cells. FcRn maintains the half-life of IgG by binding and trafficking constitutively internalized IgG back to the cell surface. Binding of both Fc and serum albumin by FcRn occurs in the early endosome at pH 6.0, followed by sorting of the FcRn into vesicles, which traffic the FcRn-bound IgG or albumin back to the cell surface where FcRn rapidly releases the IgG or albumin at pH 7.4. This trafficking cycle maintains the half-life of IgG and albumin by recycling both into the circulation and preventing trafficking to the lysosomes for degradation. FcRn also captures internalized IgG Fc in epithelial cells and transports them bidirectionally to the opposing apical or basolateral membranes. This function allows IgG to traffic to the lumen of organs such as the gastrointestinal tract or the transport of IgG or IgG-antigen complexes from the lumen to the vasculature or lymphoid tissues in the stromal layers.

In order to study the contribution of FcRn to IgG homeostasis, mice have been engineered so that parts of the light and heavy chains of FcRn have been "knocked out" so that these proteins are not expressed (Junghans et al., *Proc Natl Acad Sci USA* 93:5512, 1996). In these mice, the serum half-life and concentrations of IgG were dramatically reduced, suggesting an FcRn-dependent mechanism of IgG homeostasis. Studies in rodent models, such as the one discussed above, suggest that blockage of FcRn can increase IgG catabolism, including that of pathogenic autoantibodies, thereby inhibiting disease (e.g., an autoimmune disease) development. FcRn may also contribute to antigen presentation through trafficking of immune complexes to antigen degradation and MHC loading compartments.

The present invention provides isolated anti-FcRn antibodies that bind to human FcRn with high affinity. The anti-FcRn antibodies of the invention compete with and effectively inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies of the invention may be used in a method of treating or reducing immune complex-based activation of an immune response in a subject, such as an immune response caused by autoantibodies in an autoimmune disease.

IV. Vectors, Host Cells, and Antibody Production

The anti-FcRn antibodies of the invention can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin.

Nucleic Acid Vector Construction and Host Cells

A nucleic acid sequence encoding the amino acid sequence of an anti-FcRn antibody of the invention may be prepared by a variety of methods known in the art. These methods include, but are not limited to, oligonucleotide-mediated (or site-directed) mutagenesis and PCR mutagenesis. A nucleic acid molecule encoding an anti-FcRn antibody of the invention may be obtained using standard techniques, e.g., gene synthesis. Alternatively, a nucleic acid molecule encoding a wild-type anti-FcRn antibody may be mutated to contain specific amino acid substitutions using standard techniques in the art, e.g., QuikChange™ mutagenesis. Nucleic acid molecules can be synthesized using a nucleotide synthesizer or PCR techniques.

Nucleic acid sequences encoding anti-FcRn antibodies of the invention may be inserted into a vector capable of replicating and expressing the nucleic acid molecules in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells are used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In other embodiments, E. coli cells are used as host cells for the invention. Examples of E. coli strains include, but are not limited to, E. coli 294 (ATCC® 31,446), E. coli λ 1776 (ATCC® 31,537, E. coli BL21 (DE3) (ATCC® BAA-1025), and E. coli RV308 (ATCC® 31,608). Different host cells have characteristic and specific mechanisms for the posttranslational processing and modification of protein products. Appropriate cell lines or host systems may be chosen to ensure the correct modification and processing of the anti-FcRn antibody expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (Methods in Molecular Biology), Humana Press; 2nd ed. 2004 (Jul. 20, 2004) and Vladimir Voynov and Justin A. Caravella (eds.) *Therapeutic Proteins: Methods and Protocols* (Methods in Molecular Biology) Humana Press; 2nd ed. 2012 (Jun. 28, 2012).

Protein Production, Recovery, and Purification

Host cells used to produce the anti-FcRn antibodies of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. An anti-FcRn antibody of the invention may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see *Process Scale Purification of Antibodies*, Uwe Gottschalk (ed.) John Wiley & Sons, Inc., 2009). In some instances, an anti-FcRn antibody can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein.

Alternatively, anti-FcRn antibodies of the invention can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the anti-FcRn antibody of the invention. The vector, once inside a cell of the subject (e.g., by transformation, transfection, electroporation, calcium phosphate precipitation, direct microinjection, infection, etc) will promote expression of the anti-FcRn antibody, which is then secreted from the cell. If treatment of a disease or disorder is the desired outcome, no further action may be required. If collection of the protein is desired, blood may be collected from the subject and the protein purified from the blood by methods known in the art.

V. Pharmaceutical Compositions and Preparations

The invention features pharmaceutical compositions that include one or more anti-FcRn antibodies described herein. In some embodiments, pharmaceutical compositions of the invention contain one or more antibodies of the invention, e.g., N022-N024, N026, and N027, as the therapeutic proteins. In other embodiments, pharmaceutical compositions of the invention containing one or more antibodies of the invention, e.g., N022-N024, N026, and N027, may be used in combination with other agents (e.g., therapeutic biologics and/or small molecules) or compositions in a therapy. In addition to a therapeutically effective amount of the antibody, the pharmaceutical compositions may contain one or more pharmaceutically acceptable carriers or excipients, which can be formulated by methods known to those skilled in the art.

Acceptable carriers and excipients in the pharmaceutical compositions are nontoxic to recipients at the dosages and concentrations employed. Acceptable carriers and excipients may include buffers, antioxidants, preservatives, polymers, amino acids, and carbohydrates. Pharmaceutical compositions of the invention can be administered parenterally in the form of an injectable formulation. Pharmaceutical compositions for injection (i.e., intravenous injection) can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006).

The pharmaceutical composition may be formed in a unit dose form as needed. The amount of active component, e.g., one or more anti-FcRn antibodies of the invention (e.g., N022-N024, N026, and N027, preferably N027 and/or N024), included in the pharmaceutical preparations is such that a suitable dose within the designated range is provided (e.g., a dose within the range of 0.01-500 mg/kg of body weight).

VI. Routes, Dosage, and Administration

Pharmaceutical compositions of the invention that contain one or more anti-FcRn antibodies (e.g., N022-N024, N026, and N027, preferably N027 and/or N024) as the therapeutic proteins may be formulated for intravenous administration, parenteral administration, subcutaneous administration, intramuscular administration, intra-arterial administration, intrathecal administration, or intraperitoneal administration. In particular, intravenous administration is preferred. The pharmaceutical composition may also be formulated for, or administered via, oral, nasal, spray, aerosol, rectal, or vaginal administration. For injectable formulations, various effective pharmaceutical carriers are known in the art.

The dosage of the pharmaceutical compositions of the invention depends on factors including the route of administration, the disease to be treated, and physical characteristics, e.g., age, weight, general health, of the subject. Typically, the amount of an anti-FcRn antibody of the invention (e.g., any one of N022-N024, N026, and N027, preferably N027 or N024) contained within a single dose may be an amount that effectively prevents, delays, or treats the disease without inducing significant toxicity. A pharmaceutical composition of the invention may include a dosage of an anti-FcRn antibody of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 1 to about 100 mg/kg and, in a more specific embodiment, about 1 to about 50 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 1-100 mg/kg, e.g., 1-50 mg/kg. Pharmaceutical compositions of the invention that contain an anti-FcRn antibody (e.g., any one of N022-N024, N026, and N027, preferably N027 or N024) may be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines.

VII. Indications

The blockade of human FcRn by anti-FcRn antibodies of the invention may be of therapeutic benefit in diseases that are driven by IgG autoantibodies. The ability of FcRn blockade to induce overall IgG catabolism and removal of multiple species of autoantibodies without perturbing serum albumin, small circulating metabolites, or lipoproteins offers a method to expand the utility and accessibility of an autoantibody removal strategy to patients with autoantibody-driven autoimmune disease pathology. While the invention is not bound by theory, the dominant mechanism of action of an anti-FcRn antibody of the invention may be to increase the catabolism of pathogenic autoantibodies in circulation and decrease autoantibody and immune complex deposition in affected tissues.

The pharmaceutical compositions and methods of the invention containing one or more anti-FcRn antibodies (e.g., N022-N024, N026, and N027, preferably N027 and/or N024) are useful to promote catabolism and clearance of pathogenic antibodies, e.g., IgG and IgG autoantibodies in a subject, to reduce the immune response, e.g., to block immune complex-based activation of the immune response in a subject, and to treat immunological conditions or diseases in a subject. In particular, the pharmaceutical compositions and methods of the invention are useful to reduce or treat an immune complex-based activation of an acute or chronic immune response. The acute immune response may be activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dialated cardiomyopathy, and serum sickness. The chronic immune response may be activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis.

In some embodiments, the pharmaceutical compositions and methods of the invention are useful to reduce or treat an immune response activated by an autoimmune disease. The autoimmune disease may be selected from the group consisting of alopecia areata, ankylosing spondylitis, antiphospholipid syndrome, Addison's disease, hemolytic anemia, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In particular, the pharmaceutical compositions and methods of the invention are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica.

EXAMPLES

Example 1—Antibody Production

IgG heavy and light chain nucleic acid molecules were cloned in vector pCDNA 3.3 using osteonectin secretion signals. HEK 293F cells were grown in Expi293 media at 37° C. with 8% $CO_2$. Cells were transfected at a density of $3 \times 10^6$/ml with 1 mg total DNA per liter. Enhancers were added on days 2 and 3 following manufacturer's directions and the cells were cultured until day 5 or 6 before cell viability dropped to below 50% to 60%. The cells were then spun out by centrifugation and the spent media was sterile filtered and stored at 4° C. until antibody purification. Antibodies were purified by a two-column procedure: POROS Protein A chromatography followed by POROS HS-50 cation exchange chromatography. The former separated most of the host cell proteins from the expressed antibodies while the latter removed the heavy chain dimers, light chain dimers, and half antibodies, as well as higher molecular weight species. The fractions from the HS-50 cation exchange column were pooled based on an SDS-PAGE gel analysis to maximize purity of the full length antibodies. The collected fractions were put over a Sephadex G50 buffer exchange column equilibrated in PBS at pH 7.2. The peak fractions were pooled and concentrated to greater than 10 mg/ml using 30 kDa spin concentrators and frozen at −30° C. in 2 mg and 5 mg aliquots. The final protein samples were checked for purity by SDS-PAGE.

Example 2—Binding Affinities

Through affinity maturation, we identified more than 100 anti-FcRn antibodies having binding affinities to human FcRn with a $K_D$ in the sub-micromolar range. Five antibodies (N022-N024, N026, and N027) were selected for further characterization. Surface Plasmon Resonance (SPR) was used to determine the on- and off-rates ($k_a$ and $k_d$, respectively) for each of these five antibodies. Briefly, a Bio-Rad GLC sensor chip was inserted into the ProteOn XPR 36 and air initialized. After initialization the running buffer was switched to freshly prepared buffer, either HBSP+ (0.01 M HEPES, 0.15 M NaCl, 0.05% P20, pH 7.4) or Sodium Phosphate Buffer (0.02 M Sodium Phosphate, 0.15 M NaCl, 0.05% P20, pH 6.0) as appropriate, which was used for the remainder of the assay and for all dilutions. The chip was preconditioned using one injection each of 0.5% SDS, 50 mM NaOH and 10 mM HCl at 30 µl/min for 60 seconds (s). A mouse anti-Human Fc mAb from GE Healthcare (BR100839) was diluted to 10 µg/ml in 10 mM acetate buffer pH 5.0 and approximately 5,700 response units (RU) was immobilized using standard amine coupling chemistry in the horizontal orientation onto a GLC sensor chip. The anti-hFcRn mAbs to be tested were captured onto the surface in the vertical orientation, with the goal of immobilizing approximately 200 response units (RU) per interaction spot. The rhFcRn was diluted in a five-point three-fold dilution series starting at 1.25 µg/ml, leaving one lane as buffer-only for a double reference. The analyte was flowed across the sensor surface in the horizontal orientation at 100 µl/min for 240 s with a 3,600 s dissociation time. Regeneration was accomplished by injecting 3M $MgCl_2$ at 100 µl/min for 30 s in both the horizontal and vertical directions. These procedures were repeated for all ligands.

Data analysis was conducted using the ProteOn Manager software. Each interaction step was adjusted for the Y and X direction using the Auto Process tool, followed by interspot channel referencing to remove non-specific interactions and blank lane double referencing to remove assay drift. The data was fit using the Langmuir 1:1 kinetic model with a grouped Rmax. The $k_a$, $k_d$ and $K_D$ values obtained from ProteOn Manager in a single run were averaged and their percent CV was calculated in Microsoft Excel when the N was three or greater.

Table 3 shows that five anti-FcRn antibodies of the invention, N022, N022, N024, N026, and N027, all bind with high affinity to human FcRn at pH 7.4. The equilibrium dissociation constant, $K_D$, of the anti-FcRn antibodies of the invention ranged from 19.4 pM (N027) to 36.5 pM (N026) for binding to human FcRn at pH 7.4. Table 3 also shows the rapid on-rates and slow off-rates of the five anti-FcRn antibodies. At pH 7.4, the on-rates were in the range of 0.93-1.42×10⁶ 1/Ms for binding to human FcRn. The off-rates were in the range of 2.31-4.44×10⁶ 1/s.

TABLE 3

| | $k_a$ (1/Ms) | $k_d$ (1/s) | $K_D$ (M) | $R_{max}$ | Chi2 | $K_D$ (pM) |
|---|---|---|---|---|---|---|
| N022 | 1.42E+06 | 4.42E−05 | 3.10E−11 | 146.93 | 7.65 | 31 |
| N023 | 9.27E+05 | 2.91E−05 | 3.14E−11 | 193.43 | 5.26 | 31.4 |
| N024 | 1.13E+06 | 4.03E−05 | 3.55E−11 | 181.17 | 6.12 | 35.5 |
| N026 | 1.22E+06 | 4.44E−05 | 3.65E−11 | 163.9 | 5.68 | 36.5 |
| N027 | 1.19E+06 | 2.31E−05 | 1.94E−11 | 211.33 | 7.81 | 19.4 |

Example 3—IgG Competition

The ability of anti-FcRn antibodies of the invention to compete with IgG for binding to human or cynomolgus monkey FcRn was evaluated on human embryonic kidney (HEK) 293 cells ectopically expressing cell surface, glycophosphatidylinositol (GPI)-linked FcRn. Human and cynomolgus monkey FcRn alpha amino acid sequences exhibit 97.5% sequence identity. Nine amino acid residues of 355 are different between human and cynomolgus monkey FcRn alpha, but none are in the epitope-mapped binding region. The level of cell-bound IgG was determined using 66 nM of fluorescent probe-labeled, non-specific IgG. The binding of IgG to cell surface FcRn was done at pH 6.0, which allows the Fc portion of IgG to interact with FcRn. As shown in FIG. 1, the amount of cell-bound IgG significantly decreased as the concentration of the anti-FcRn antibody (N022-N024, N026, or N027) increased. The binding of IgG was inhibited in a concentration- and saturation-dependent manner by each of the five exemplary anti-FcRn antibodies of the invention, demonstrating the ability of the anti-FcRn antibodies, N022-N024, N026, and N027, to effectively compete with and inhibit binding of IgG to FcRn at pH 6.0. The EC50 values of the antibodies ranged between 2 and 6 nM.

Example 4—Effect of Anti-FcRn Antibodies on IgG Catabolism in Mice

Figure 2:
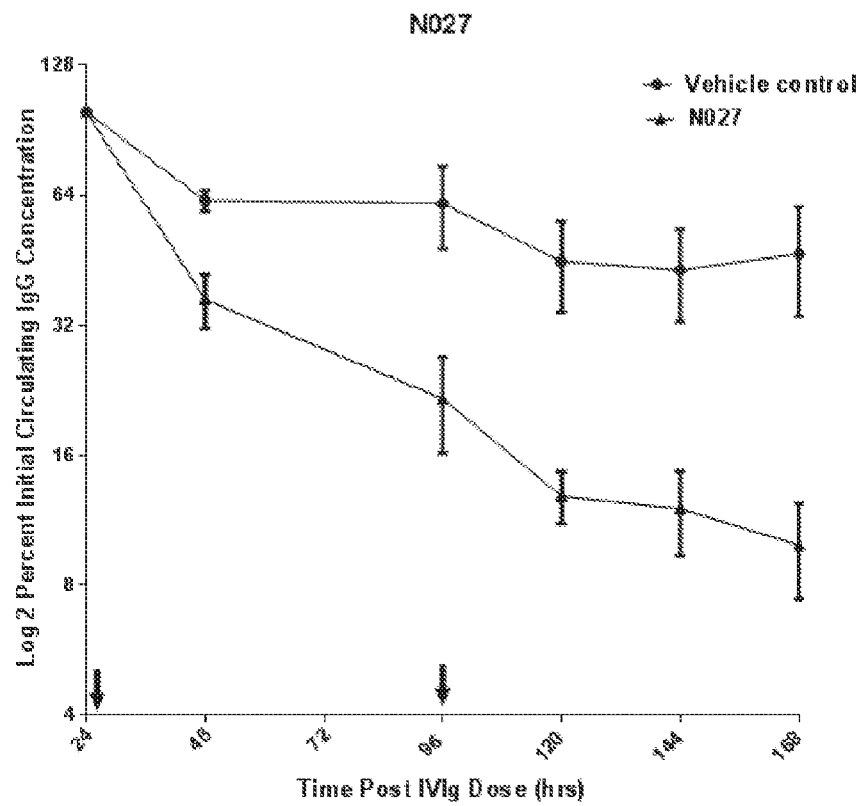
FIG. 2 includes graphs that show the effects of antibodies N023, N024, N026, and N027 on IgG catabolism in mice.
Figure 2:
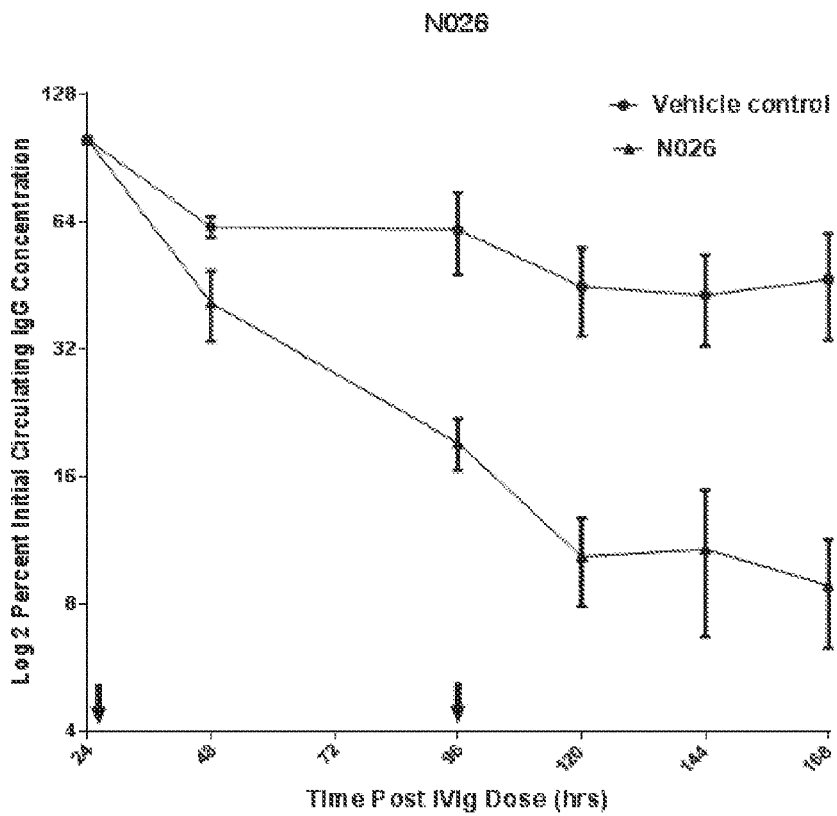

To measure the effect of the anti-FcRn antibodies of the invention on IgG catabolism in vivo, human FcRn transgenic mouse strain FcRn−/−hFcRn (32) Tg mice, which lacks mouse FcRn but expresses human FcRn in a tissue distribution similar to the endogenous mouse and human FcRn, was used. FcRn−/−hFcRn (32) Tg mice injected with 500 mg/kg human IgG on day 0 were administered a single dose of an anti-FcRn antibody at 10 mg/kg on days 1 and 4. As shown in FIG. 2, the catabolism of IgG was increased by the administration of anti-FcRn antibodies as seen by lower levels of IgG measured over time in anti-FcRn antibody-treated mice. The activities of N024 ($K_D$=35.5 pM), N026 ($K_D$=36.5 pM), and N027 ($K_D$=19.4 pM) appeared to be to be similar at 10 mg/kg.

Example 5—In Vitro and In Vivo Functional Characterizations of Anti-FcRn Antibodies In Vitro Cellular binding affinities of the antibodies of the invention were measured on human embryonic kidney (HEK) 293 cells ectopically expressing cell surface, glycophosphatidylinositol (GPI)-linked human or cynomolgus monkey FcRn. FcRn is a type I transmembrane protein with the IgG and albumin binding domains oriented to the luminal side of endosomal membranes or to the cell surface when transported to the plasma membrane. The binding of anti-FcRn antibodies to cell surface, membrane-associated FcRn on HEK293 cells at pH 7.4 mimics binding in a physiologically-relevant environment and at the pH where only the Fab domain and not the Fc domain of the antibodies interact with FcRn. The FcRn extracellular domain was displayed on the cell surface at high density through a C-terminal engineered GPI linkage. The anti-FcRn antibodies of the invention were labeled with a fluorescent probe. The antibodies were allowed to bind for 30 minutes on ice. Cells were then washed at 4° C. and bound antibodies were detected using a fluorophore-labeled secondary antibody, e.g., a goat anti-human IgG F(ab)$_2$. The binding to human FcRn was concentration dependent and antibodies of the invention displayed EC50 values ranging from 4 to 7 nM.

Cellular binding affinities of the antibodies of the invention were also measured on endogenously expressed human FcRn. Monocytes express the highest levels of FcRn and show the highest percent positivity for FcRn expression in mouse and human blood. Monocytic cell line THP-1 was used to evaluate binding of anti-FcRn antibodies to endogenous human FcRn at pH 7.4. Since endogenous FcRn is primarily in intracellular endosomal vesicles in THP-1 cells, the cells were first permeabilized with a mild detergent and fixed prior to incubation for 30 minutes at 4° C. with anti-FcRn antibodies in the presence of bovine serum to block non-specific Fc receptor binding. This assay was able to distinguish antibodies with better binding to endogenous human FcRn. The binding of anti-FcRn antibodies to THP-1 cells is concentration dependent. All antibodies of the invention, e.g., N022-N024, N026, and N027, showed better binding affinities than IgG1. Antibody N027 displayed the highest binding affinity with an EC50 value of 3.0 nM.

The ability of anti-FcRn antibodies of the invention to compete with IgG for binding to human or cynomolgus monkey FcRn was evaluated on human embryonic kidney (HEK) 293 cells ectopically expressing cell surface, GPI-linked FcRn. The level of cell-bound IgG was determined using fluorescent probe-labeled, non-specific IgG. The binding of IgG to cell surface FcRn was done at pH 6.0, which allows the Fc portion of IgG to interact with FcRn. As shown in Example 3 and FIG. 1, the amount of cell-bound IgG significantly decreased as the concentration of the anti-FcRn antibody increased. The binding of IgG was inhibited in a concentration- and saturation-dependent manner by each of the five exemplary anti-FcRn antibodies of the invention, e.g., N022-N024, N026, and N027, demonstrating the ability of the anti-FcRn antibodies to effectively compete with and inhibit binding of IgG to FcRn at pH 6.0. The EC50 values of the antibodies ranged from 2 to 6 nM.

Epitope mapping by hydrogen-deuterium exchange of the antibodies of the invention indicated that the antibodies bind to an epitope on human FcRn located in and/or adjacent to the Fc-FcRn interaction interface, which suggests that the antibodies of the invention block IgG binding to FcRn by direction inhibition. Furthermore, the epitope-mapped binding site is distant from the albumin-binding site of FcRn, thus, serum albumin-binding should not be inhibited and serum albumin levels should not be decreased. An enzyme-linked immunosorbent assay (ELISA) was used to confirm that the antibodies of the invention do not inhibit serum albumin binding to FcRn. Soluble His-tagged extracellular domain of human FcRn was bound to the plate surface and pre-incubated with increasing concentrations of anti-FcRn antibody at pH 6.0. Horseradish peroxidase (HRP)-conjugated human serum albumin was allowed to bind to the soluble, His-tagged FcRn. None of the antibodies inhibited albumin binding to FcRn. Furthermore, in vivo experimental evidence also showed that mouse albumin levels remained constant after anti-FcRn antibody administration, indicating that albumin recycling was not disturbed by antibody binding to FcRn.

In Vivo

To test the in vivo effect of anti-FcRn antibodies of the invention on IgG catabolism, human FcRn transgenic mouse strain FcRn−/−hFcRn (32) Tg mice, which lack mouse FcRn but express human FcRn in a tissue distribution similar to that of the endogenous mouse and human FcRn, were used. FcRn−/−hFcRn (32) Tg mice injected with human IgG on day 0 were administered a single dose of an anti-FcRn antibody at 10 mg/kg on days 1 and 4. As shown in Example 3 and FIG. 2, the catabolism of IgG was increased by the administration of anti-FcRn antibodies as seen by lower levels of IgG measured over time in anti-FcRn antibody-treated mice. The activities of N024 ($K_D$=35.5 pM), N026 ($K_D$=36.5 pM), and N027 ($K_D$=19.4 pM) appeared to be to be similar at 10 mg/kg.

Figure 3:
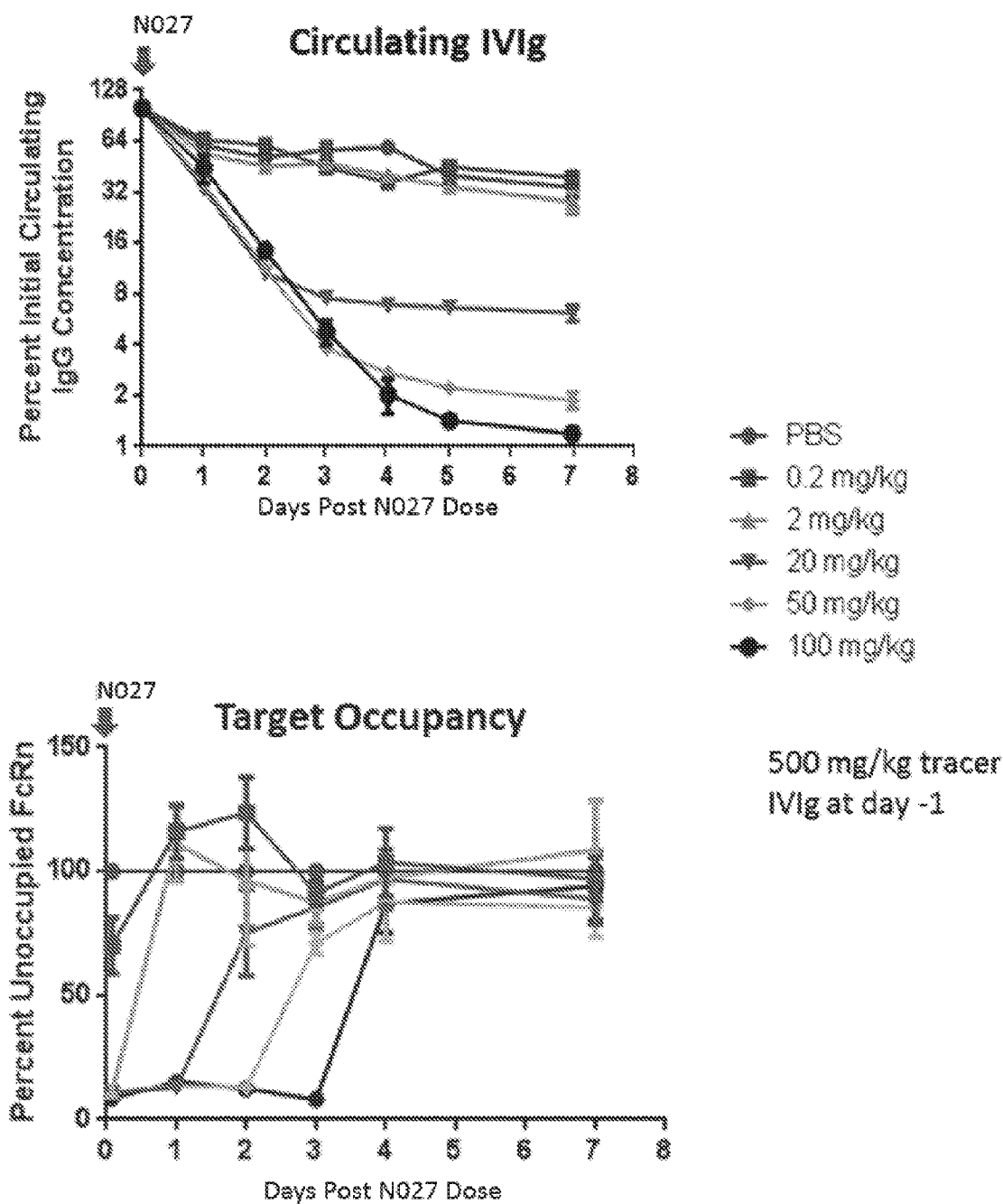
FIG. 3 includes graphs that show the dose-dependent effects of antibody N027 on IgG levels and target occupancy in mice.

Example 6—Effect of Anti-FcRn Antibodies on IgG Levels and Target Occupancy in Mice N027 was dosed intravenously (i.v.) 24 hrs after administration of 500 mg/kg IVIg (tracer) to Tg32 human FcRn (hFCGRT) transgenic, mouse FcRn (mFCGRT) knockout mice. Circulating human IgG was detected by ELISA on each day. Target occupancy was measured on each day in monocytes from lysed whole blood by fluorescence-activated cell sorting (FACS), after incubation of cells with immunophenotyping cell surface markers followed by fixation and permeabilization. Unoccupied FcRn was measured by staining with Dy650-labeled N027 (n=4 males per group). As shown in FIG. 3, IgG level and the percentage of unoccupied FcRn were decreased by the administration of N027 in a dose-dependent manner.

Figure 4:
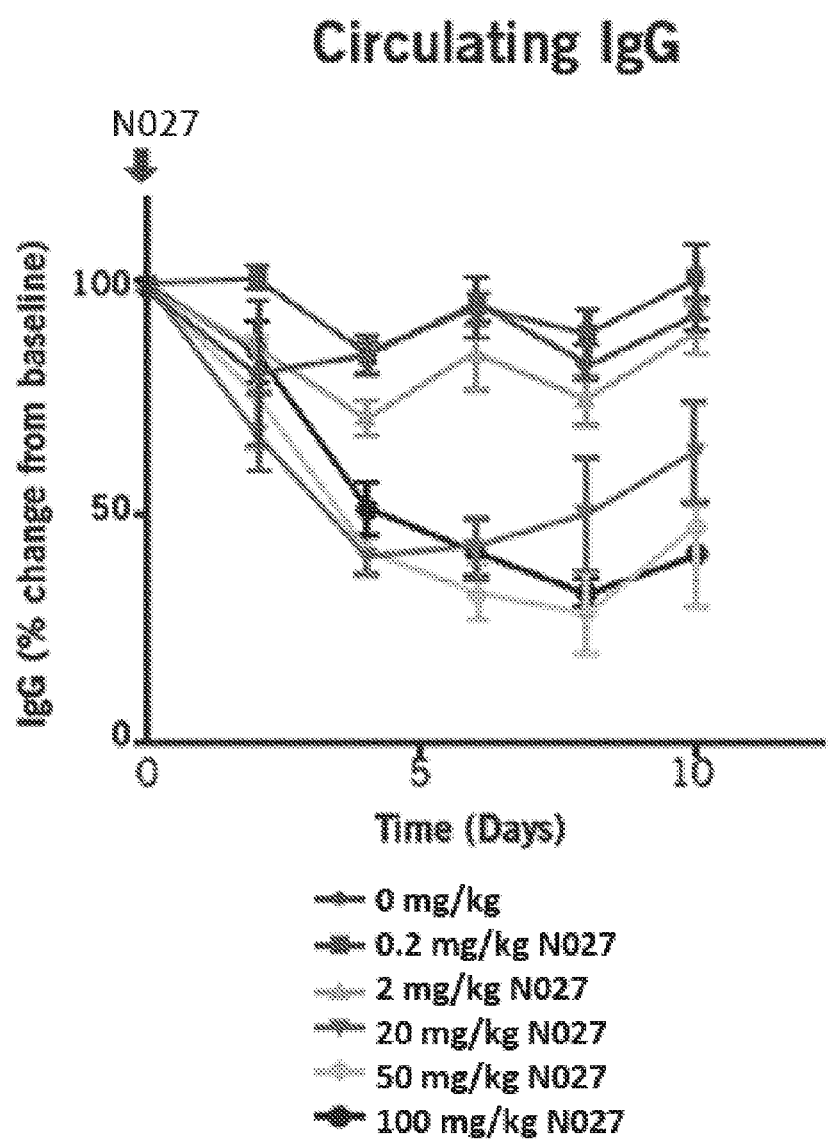
FIG. 4 includes graphs that show the selective induction of IgG catabolism and target occupancy in cynomolgus monkeys following administration of different doses of antibody N027.
Figure 4:
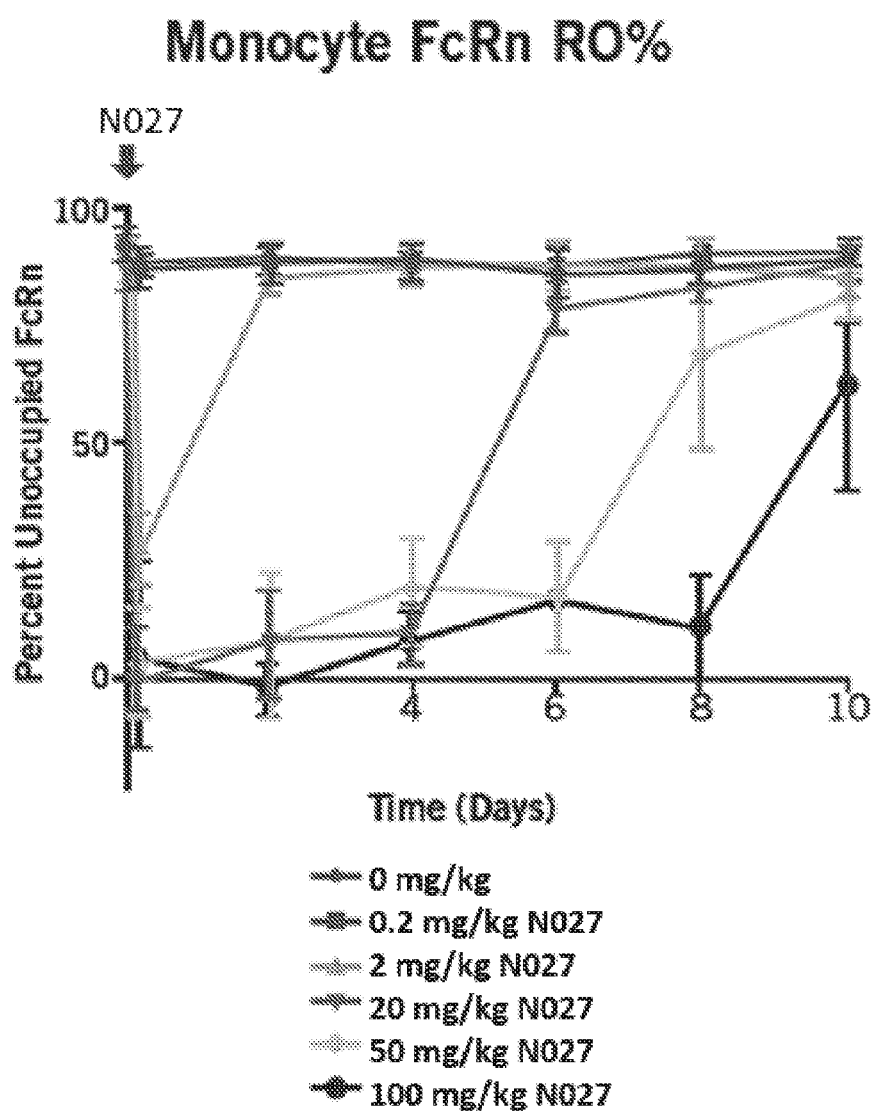
Figure 4:
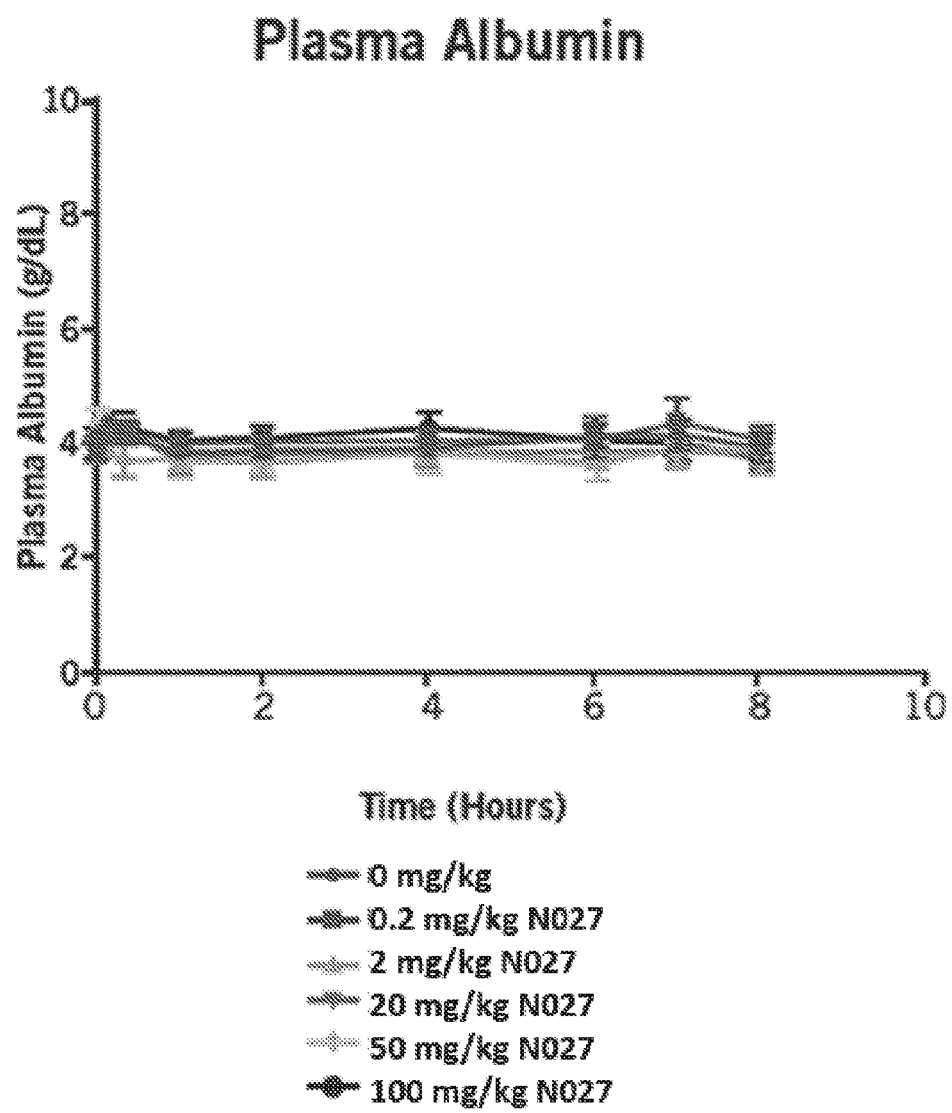

Example 7—Selective Induction of IgG Catabolism and Target Occupancy in Cynomolgus Monkeys N027 was dosed i.v. at t=0 in cynomolgus monkeys. Circulating endogenous IgG and albumin was detected by ELISA. Target occupancy was measured in monocytes from lysed whole blood by FACS, after incubation of cells with immunophenotyping cell surface markers followed by fixation and permeabilization. Unoccupied FcRn was measured by staining with Dy650-labeled N027. (n=3 males per group). As shown in FIG. 4, IgG level and the percentage of unoccupied FcRn were decreased by the administration of N027 in a dose-dependent manner, while plasma albumin level stayed unchanged.

Example 8—Biodistribution of N027 in Mice

Figure 5:
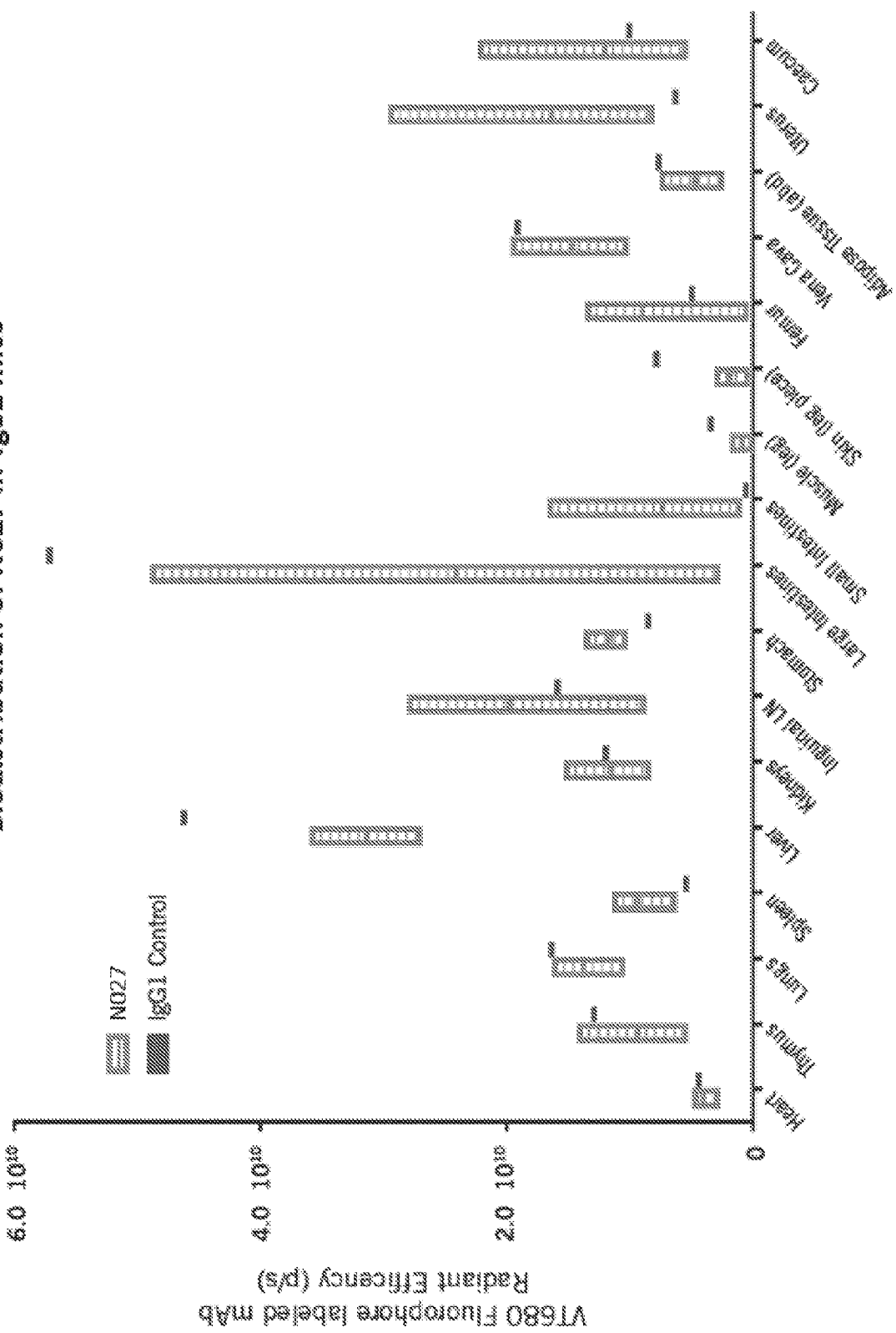
FIG. 5 includes a graph that shows the biodistribution of N027 in mice.

N027 or isotype human IgG1 control antibody labeled with fluorophore (VT680) was administered i.v. to Tg32 human FcRn transgenic, mouse FcRn knockout mice at 30 mg/kg. Levels of labeled antibody were measured in individual organs by quantitative ex vivo optical imaging. FIG. 5 shows the biodistribution of N027 in various organs in mice.

Example 9—Efficacy of N027 in Mouse Collagen Antibody-Induced Arthritis

Figure 6:
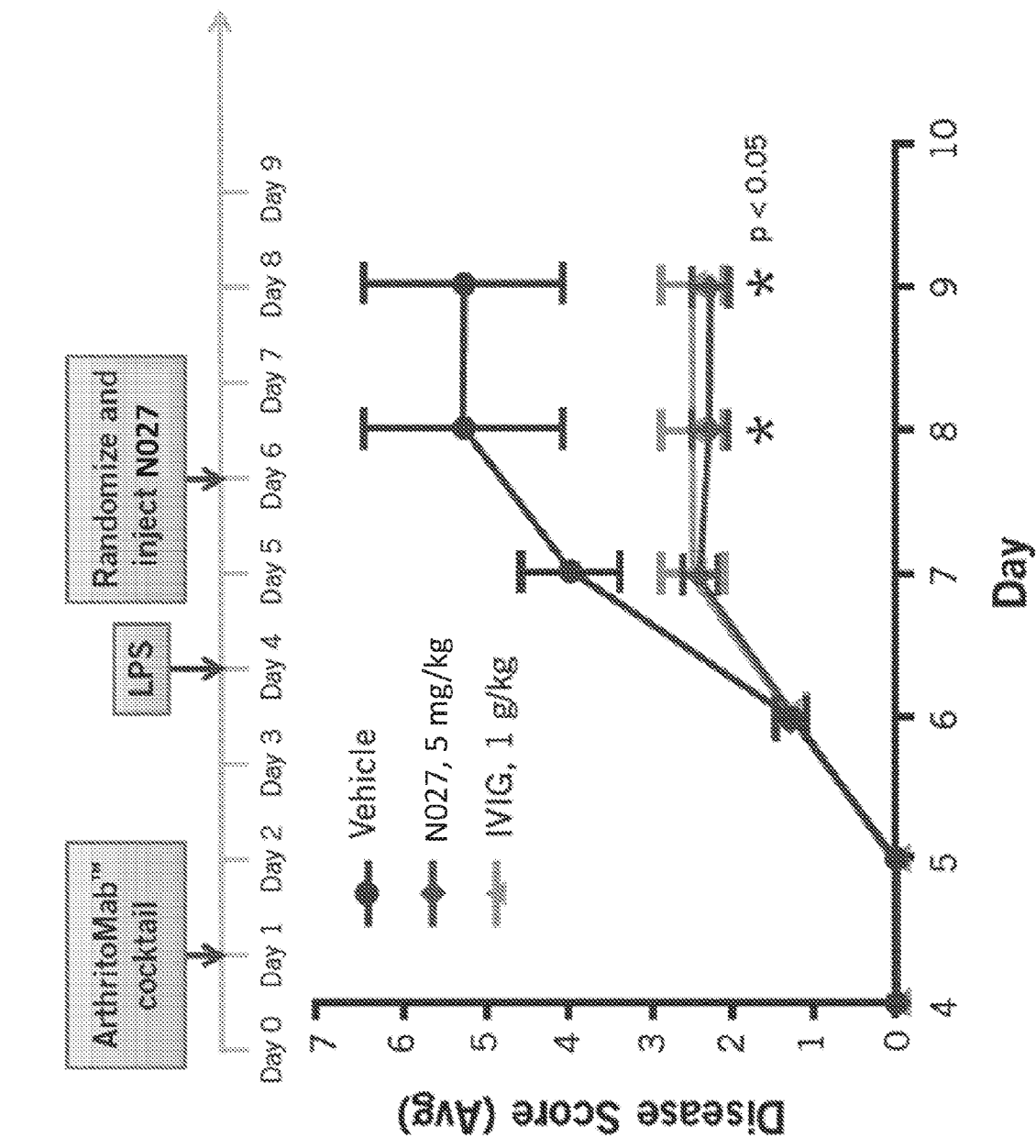
FIG. 6 includes an experimental timeline and a graph that shows the efficacy of N027 in a mouse collagen antibody-induced arthritis model.

Collagen antibody-induced arthritis was induced in Tg32 human FcRn transgenic, mouse FcRn knockout mice by intraperitoneal (i.p.) injection of ArthritoMab™ cocktail (MD Biosciences) on day 1 and inflammatory disease activity induced with 100 μg LPS i.p. on day 4. N027 was dosed therapeutically i.v. at 5 mg/kg (arrow), on day 6 post disease induction and randomization. IVIG at 1 g/kg (positive control group) or vehicle-PBS (negative control) were dosed on day 6 after randomization (n=5 per group). As shown in FIG. 6, N027 potently inhibits collagen antibody-induced arthritis in human transgenic FcRn mice when dosed therapeutically.

Example 10—Efficacy of N027 in Mouse Chronic Idiopathic Thrombocytopenia Purpura (ITP)

Figure 7:
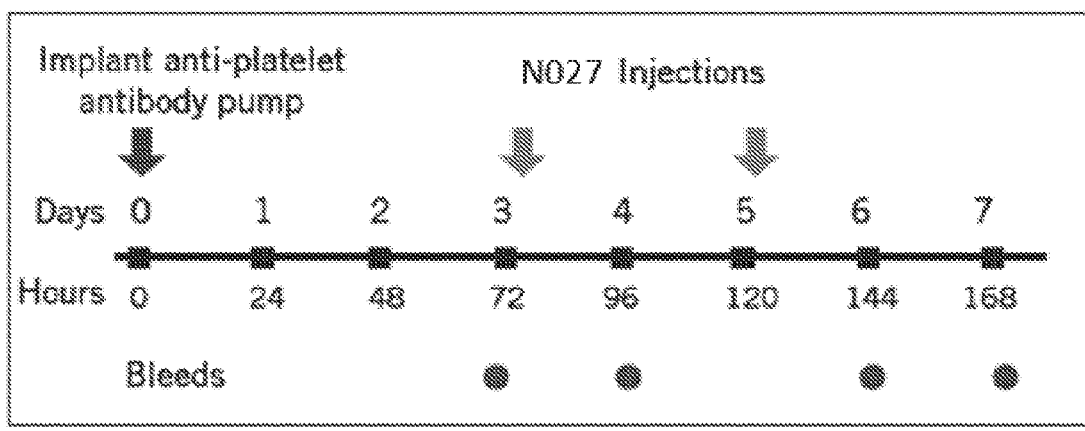
FIG. 7 includes an experimental timeline and two graphs that show the efficacy of N027 in a mouse chronic idiopathic thrombocytopenia purpura (ITP) model.
Figure 7:
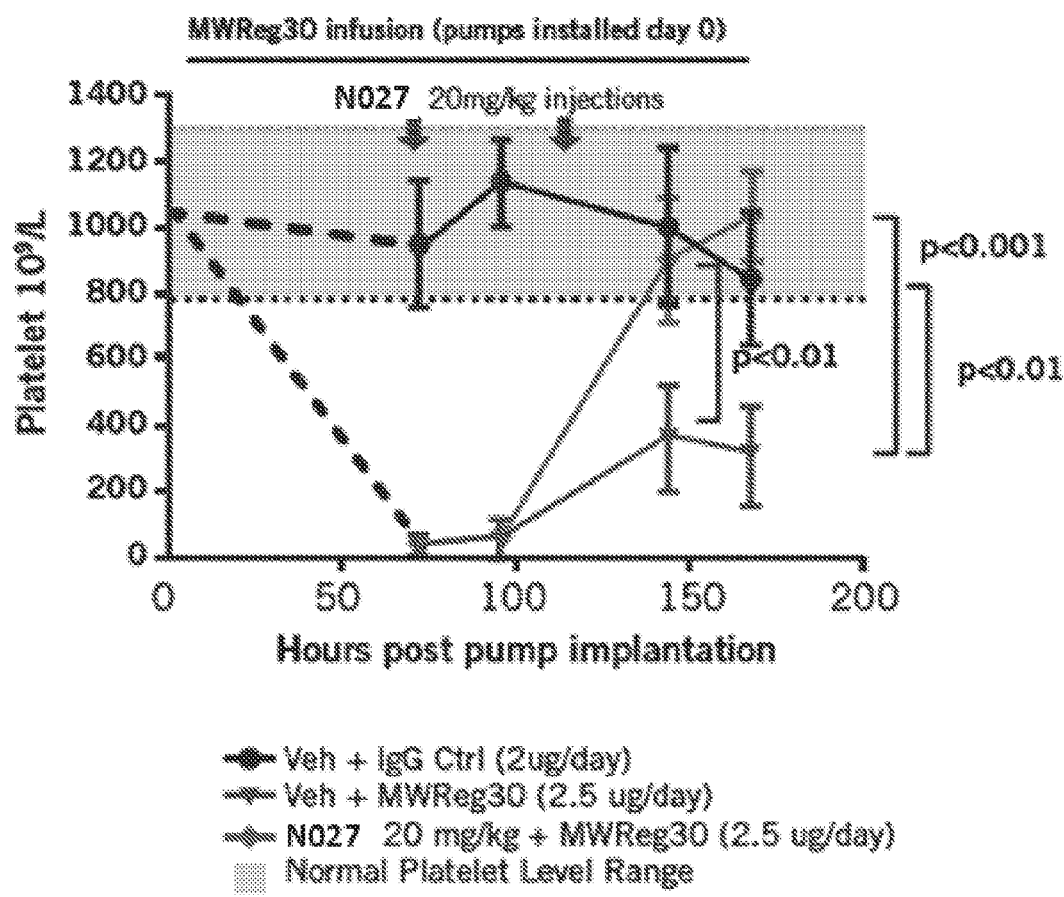
Figure 7:
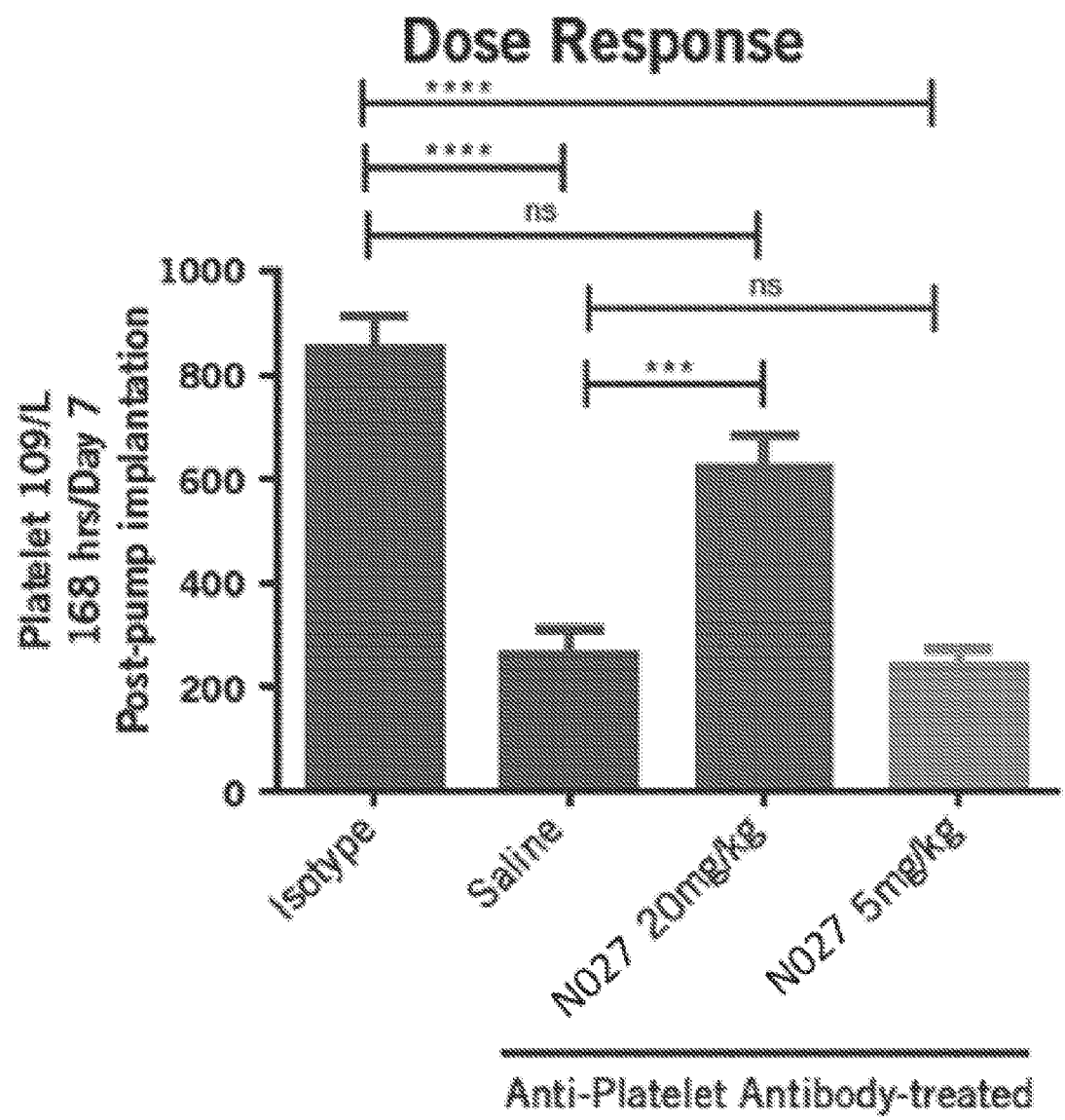

Thrombocytopenia was induced in Tg32 human FcRn (hFCGRT) transgenic, mouse FcRn (mFCGRT) knockout mice by continuous infusion of anti-platelet antibody (anti-CD41, MWReg30) subcutaneous (s.c.) miniosmotic pump. Circulating platelet levels were decreased to 300×109/L or less by 72 hrs (Day 3) after pump implantation. N027 was dosed therapeutically i.v. 72 hrs (day 3) and 120 hrs (Day 5) post-pump implantation (A, n=4 per group; B, n=7 per group). FIG. 7 shows the effects of N027 on platelet levels in mice having thrombocytopenia.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

SEQUENCE LISTING

```
<160> NUMBER OF SEQ ID NOS: 24

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Thr Gly Thr Gly Ser Asp Val Gly Ser Tyr Asn Leu Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Gly Asp Ser Glu Arg Pro Ser
1               5

<210> SEQ ID NO 3
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Ser Ser Tyr Ala Gly Ser Gly Ile Tyr Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Thr Tyr Ala Met Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic construct

<400> SEQUENCE: 5

Asp Tyr Ala Met Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Asn Tyr Ala Met Gly
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Ser Ile Gly Ser Ser Gly Ala Gln Thr Arg Tyr Ala Asp Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic construct

<400> SEQUENCE: 8

Ser Ile Gly Ala Ser Gly Ser Gln Thr Arg Tyr Ala Asp Ser
1               5                   10

<210> SEQ ID NO 9
<211> LENGTH: 14
```

```
<212> TYPE: PRT
<213> ORGANISM: Artificial Sequence
<220> FEATURE:
<223> OTHER INFORMATION: Synthetic construct

<400> SEQUENCE: 9

Ser Ile Gly Ala Ser Gly Ala Gln Thr Arg Tyr Ala Asp Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct

<400> SEQUENCE: 10

Ser Ile Gly Ala Ser Gly Gly Gln Thr Arg Tyr Ala Asp Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic construct

<400> SEQUENCE: 11

Leu Ala Ile Gly Asp Ser Tyr
1               5

<210> SEQ ID NO 12
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is a polar or hydrophobic amino acid, e.g.
      Thr, Ala, Ser, or Ile
<220> FEATURE:
<221> NAME/KEY: MISC_FEATURE
<222> LOCATION: (12)..(12)
<223> OTHER INFORMATION: Xaa is a hydrophobic amino acid, e.g. Leu or
      Ile

<400> SEQUENCE: 12

Xaa Gly Thr Gly Ser Asp Val Gly Ser Tyr Asn Xaa Val Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is a polar amino acid, e.g. Ser, Asn, or
      Thr
<220> FEATURE:
<221> NAME/KEY: MISC_FEATURE
<222> LOCATION: (4)..(4)
<223> OTHER INFORMATION: Xaa is a polar or acidic amino acid, e.g. Gln,
      Glu, or Asn

<400> SEQUENCE: 13
```

```
Gly Asp Xaa Xaa Arg Pro Ser
1               5
```

<210> SEQ ID NO 14
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is a polar or hydrophobic amino acid, e.g.
      Cys, Ser, Ile, or Tyr
<220> FEATURE:
<221> NAME/KEY: MISC_FEATURE
<222> LOCATION: (4)..(4)
<223> OTHER INFORMATION: Xaa is a hydrophobic amino acid, e.g. Ala or
      Val

<400> SEQUENCE: 14

```
Xaa Ser Tyr Xaa Gly Ser Gly Ile Tyr Val
1               5                   10
```

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is a polar or acidic amino acid, e.g. Glu,
      Thr, Asp, or Asn

<400> SEQUENCE: 15

```
Xaa Tyr Ala Met Gly
1               5
```

<210> SEQ ID NO 16
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is a polar or hydrophobic amino acid, e.g.
      Ser or Ala
<220> FEATURE:
<221> NAME/KEY: MISC_FEATURE
<222> LOCATION: (7)..(7)
<223> OTHER INFORMATION: Xaa is Gly, Ser, or Ala
<220> FEATURE:
<221> NAME/KEY: MISC_FEATURE
<222> LOCATION: (10)..(10)
<223> OTHER INFORMATION: Xaa is a basic amino acid, e.g. Gly, Ser, or
      Ala

<400> SEQUENCE: 16

```
Ser Ile Gly Xaa Ser Gly Xaa Gln Thr Xaa Tyr Ala Asp Ser
1               5                   10
```

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (3)..(3)
<223> OTHER INFORMATION: Xaa is a hydrophobic or basic amino acid, e.g.
      Ile, Leu, or His
<220> FEATURE:
<221> NAME/KEY: MISC_FEATURE
<222> LOCATION: (4)..(4)
<223> OTHER INFORMATION: Xaa is Gly, Ser, Asp, Gln, or His

<400> SEQUENCE: 17

Leu Ala Xaa Xaa Asp Ser Tyr
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is a polar or hydrophobic amino acid, e.g.
      Ser or Ala
<220> FEATURE:
<221> NAME/KEY: MISC_FEATURE
<222> LOCATION: (7)..(7)
<223> OTHER INFORMATION: Xaa is Glu, Ser, or Ala

<400> SEQUENCE: 18

Ser Ile Gly Xaa Ser Gly Xaa Gln Thr Arg Tyr Ala Asp Ser
1               5                   10

<210> SEQ ID NO 19
<211> LENGTH: 216
<212> TYPE: PRT
<213> ORGANISM: Artificial Sequence
<220> FEATURE:
<223> OTHER INFORMATION: Synthetic Construct

<400> SEQUENCE: 19

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

-continued

```
Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 20
<211> LENGTH: 445
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ser Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 21
<211> LENGTH: 445
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Val
            35                  40                  45

Ser Ser Ile Gly Ala Ser Gly Ser Gln Thr Arg Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 22
<211> LENGTH: 445
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 23
<211> LENGTH: 445
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Gly Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 24
<211> LENGTH: 445
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```

What is claimed is:

1. An isolated antibody that binds to human FcRn, the isolated antibody comprising: (1) a light chain variable region comprising a CDR L1, a CDR L2, and a CDR L3 and (2) a heavy chain variable region comprising a CDR H1, a CDR H2, and a CDR H3, wherein the isolated antibody is selected from the group consisting of:
   (a) an antibody wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence TYAMG (SEQ ID NO: 4), CDR H2 comprise the amino acid sequence SIGSSGAQTRYADS (SEQ ID NO: 7), and CDR H3 comprises the amino acid sequence LAIGDSY (SEQ ID NO: 11);
   (b) an antibody wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence DYAMG (SEQ ID NO: 5), CDR H2 comprise the amino acid sequence SIGASGSQTRYADS (SEQ ID NO: 8), and CDR H3 comprises the amino acid sequence LAIGDSY (SEQ ID NO: 11);
   (c) an antibody wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence NYAMG (SEQ ID NO: 6), CDR H2 comprise the amino acid sequence SIGASGAQTRYADS (SEQ ID NO: 9), and CDR H3 comprises the amino acid sequence LAIGDSY (SEQ ID NO: 11);
   (d) an antibody wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence TYAMG (SEQ ID NO: 4), CDR H2 comprise the amino acid sequence SIGASGGQTRYADS (SEQ ID NO: 10), and CDR H3 comprises the amino acid sequence LAIGDSY (SEQ ID NO: 11); and
   (e) an antibody wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence TYAMG (SEQ ID NO: 4), CDR H2 comprise the amino acid sequence SIGASGSQTRYADS (SEQ ID NO: 8) and CDR H3 comprises the amino acid sequence LAIGDSY (SEQ ID NO: 11).

2. The isolated antibody of claim 1, wherein the antibody binds human FcRn with a $K_D$ of less than or equal to that of an antibody having a light chain comprising the amino acid sequence of SEQ ID NO: 19 and a heavy chain comprising the amino acid sequence of SEQ ID NO: 23.

3. The isolated antibody of claim 1, wherein
   CDR L1 comprises the amino acid sequence TGTGSDVGSYNLVS (SEQ ID NO: 1),
   CDR L2 comprises the amino acid sequence GDSERPS (SEQ ID NO: 2),
   CDR L3 comprises the amino acid sequence SSYAGSGIYV (SEQ ID NO: 3),
   CDR H1 comprises the amino acid sequence TYAMG (SEQ ID NO: 4),
   CDR H2 comprises the amino acid sequence SIGASGSQTRYADS (SEQ ID NO: 8), and
   CDR H3 comprises the amino acid sequence LAIGDSY (SEQ ID NO: 11).

4. The isolated antibody of claim 1, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequence SSYAGSGIYV (SEQ ID NO: 3), CDR H1 comprises the amino acid sequence TYAMG (SEQ ID NO: 4), CDR H2 comprise the amino acid sequence SIGSSGAQTRYADS (SEQ ID NO: 7), and CDR H3 comprises the amino acid sequence LAIGDSY (SEQ ID NO: 11); and the light chain of comprises an amino acid sequence having at least 90% identity to

```
                                        (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS.
```

5. The isolated antibody of claim 1 or claim 4, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequences SSYAGSGIYV (SEQ ID NO: 3), CDR H1 comprises the amino acid sequence TYAMG (SEQ ID NO: 4), CDR H2 comprise the amino acid sequence SIGASGSQTRYADS (SEQ ID NO: 8), and CDR H3 comprises the amino acid sequence LAIGDSY (SEQ ID NO: 11); and
   the heavy chain comprises an amino acid sequence having at least 90% identity to (SEQ ID NO: 24)
EVQLLESGGGLVQPGGSLRLSCAASGFTFSTYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

6. An isolated antibody that binds to human FcRn selected from the group consisting of:

(a) an antibody comprising a light chain comprising the amino acid sequence (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;

and a heavy chain comprising the amino acid sequence (SEQ ID NO: 24)
EVQLLESGGGLVQPGGSLRLSCAASGFTFSTYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

(b) an antibody comprising a light chain comprising the amino acid sequence (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;

and a heavy chain comprising the amino acid sequence (SEQ ID NO: 20)
EVQLLESGGGLVQPGGSLRLSCAASGFTFSTYAMGWVRQAPGKGLEWVSS
IGSSGAQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG;

(c) an antibody comprising a light chain comprising the amino acid sequence (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;

and a heavy chain comprising the amino acid sequence (SEQ ID NO: 21)
EVQLLESGGGLVQPGGSLRLSCAASGFTFSDYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG;

(d) an antibody comprising a light chain comprising the amino acid sequence (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;

and a heavy chain comprising the amino acid sequence (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG;

and (e) an antibody comprising a light chain comprising the amino acid sequence (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and a heavy chain comprising the amino acid sequence (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

7. The isolated antibody of claim 1, wherein the antibody comprises an IgG1 heavy chain having an amino acid substitution N297A, numbered according to the EU numbering system.

8. A pharmaceutical composition comprising an isolated antibody of claim 1 and one or more pharmaceutically acceptable carriers or excipients.

9. An isolated antibody that binds to human FcRn, the antibody comprising a light chain comprising CDR L1, CDR L2 and CDR L3 and a heavy chain comprising CDR H1, CDR H2 and CDR H3, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequences SSYAGSGIYV (SEQ ID NO: 3), CDR H1 comprises the amino acid sequence TYAMG (SEQ ID NO: 4), CDR H2 comprise the amino acid sequence SIGSS-GAQTRYADS (SEQ ID NO: 7), and CDR H3 comprises the amino acid sequence LAIGDSY (SEQ ID NO: 11); and the heavy chain comprises an amino acid sequence having at least 90% identity to (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

10. An isolated antibody that binds to human FcRn, the antibody comprising a light chain comprising CDR L1, CDR L2 and CDR L3 and a heavy chain comprising CDR H1, CDR H2 and CDR H3, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequences SSYAGSGIYV (SEQ ID NO: 3), CDR H1 comprises the amino acid sequence DYAMG (SEQ ID NO: 5), CDR H2 comprise the amino acid sequence SIGASGSQTRYADS (SEQ ID NO: 8), and CDR H3 comprises the amino acid sequence LAIGDSY (SEQ ID NO: 11); and the heavy chain comprises an amino acid sequence having at least 90% identity to (SEQ ID NO: 21)
EVQLLESGGGLVQPGGSLRLSCAASGFTFSDYAMGWVRQAPGKGLEWVS

SIGASGSQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPG.

11. An isolated antibody that binds to human FcRn, the antibody comprising a light chain comprising CDR L1, CDR L2 and CDR L3 and a heavy chain comprising CDR H1, CDR H2 and CDR H3, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequences SSYAGSGIYV (SEQ ID NO: 3), CDR H1 comprises the amino acid sequence NYAMG (SEQ ID NO: 6), CDR H2 comprise the amino acid sequence SIGAS-GAQTRYADS (SEQ ID NO: 9), and CDR H3 comprises the amino acid sequence LAIGDSY (SEQ ID NO: 11); and the heavy chain comprises an amino acid sequence having at least 90% identity to

```
                                                   (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

12. An isolated antibody that binds to human FcRn, the antibody comprising a light chain comprising CDR L1, CDR L2 and CDR L3 and a heavy chain comprising CDR H1, CDR H2 and CDR H3, wherein CDR L1 comprises the amino acid sequence TGTGSDVGSYNLVS (SEQ ID NO: 1), CDR L2 comprises the amino acid sequence GDSERPS (SEQ ID NO: 2), CDR L3 comprises the amino acid sequences SSYAGSGIYV (SEQ ID NO: 3), CDR H1 comprises the amino acid sequence TYAMG (SEQ ID NO: 4), CDR H2 comprise the amino acid sequence SIGASGGQTRYADS (SEQ ID NO: 10), and CDR H3 comprises the amino acid sequence LAIGDSY (SEQ ID NO: 11); and the heavy chain comprises an amino acid sequence having at least 90% identity to

```
                                                   (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

13. The isolated antibody of claim 9, wherein the heavy chain comprises an amino acid sequence having at least 95% identity to

```
                                                   (SEQ ID NO: 20)
EVQLLESGGGLVQPGGSLRLSCAASGFTFSTYAMGWVRQAPGKGLEWVS

SIGSSGAQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ
```

```
YASTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPG.
```

14. The isolated antibody of claim 10, wherein the heavy chain comprises an amino acid sequence having at least 95% identity to

```
                                                   (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

15. The isolated antibody of claim 11, wherein the heavy chain comprises an amino acid sequence having at least 95% identity to

```
                                                   (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

16. The isolated antibody of claim 12, wherein the heavy chain comprises an amino acid sequence having at least 95% identity to

```
                                                   (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR
```

-continued
```
VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

17. The isolated antibody of claim 5, wherein the heavy chain comprises an amino acid sequence having at least 95% identity to

```
                                        (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

18. The isolated antibody of claim 1 which is a human IgG1 antibody lacking effector function.

19. The isolated antibody of any of claims 2, 3, 4, 6, 7, 9-16 lacking effector function.

* * * * *

UNITED STATES PATENT AND TRADEMARK OFFICE
CERTIFICATE OF CORRECTION

PATENT NO. : 10,676,526 B2
APPLICATION NO. : 15/546870
DATED : June 9, 2020
INVENTOR(S) : Marilyn Kehry et al.

It is certified that error appears in the above-identified patent and that said Letters Patent is hereby corrected as shown below:

In the Claims

Claim 5, Column 60, Line 56, replace "or claim 4" with --or claim 3--.

Signed and Sealed this
Second Day of April, 2024

Katherine Kelly Vidal
*Director of the United States Patent and Trademark Office*